United States Patent
Carrison

(10) Patent No.: US 9,750,509 B2
(45) Date of Patent: Sep. 5, 2017

(54) RADIALLY ADJUSTABLE TISSUE REMOVAL DEVICE

(71) Applicant: BOSTON SCIENTIFIC SCIMED, INC., Maple Grove, MN (US)

(72) Inventor: Harold F. Carrison, Pleasanton, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 766 days.

(21) Appl. No.: 13/777,409

(22) Filed: Feb. 26, 2013

(65) Prior Publication Data
US 2013/0172919 A1 Jul. 4, 2013

Related U.S. Application Data

(63) Continuation of application No. 10/793,694, filed on Mar. 3, 2004.

(51) Int. Cl.
*A61B 17/16* (2006.01)
*A61B 17/221* (2006.01)
(Continued)

(52) U.S. Cl.
CPC ........ *A61B 17/1671* (2013.01); *A61B 17/221* (2013.01); *A61B 17/32002* (2013.01);
(Continued)

(58) Field of Classification Search
CPC A61B 2017/320004; A61B 17/320758; A61B 17/32002; A61B 17/221; A61B 17/1671
(Continued)

(56) References Cited

U.S. PATENT DOCUMENTS 3,732,858 A 5/1973 Banko
4,733,663 A 3/1988 Farley
(Continued)

FOREIGN PATENT DOCUMENTS

| EP | 0086048 | 8/1983 |
|---|---|---|
| WO | 02/03870 | 1/2002 |
| WO | 93/09731 | 5/2003 |

OTHER PUBLICATIONS

Patent Prosecution File History for Related U.S. Appl. No. 10/793,693, filed Mar. 3, 2004, including: Non final Office action mailed Nov. 7, 2006, for related U.S. Appl. No. 10/793,693, Inventor Harold F. Carrison et al. (11 pages); Amendment Response for Non final Office action mailed Nov. 7, 2006, submitted on Jan. 25, 2007, for related U.S. Appl. No. 10/793,693, Inventor Harold F. Carrison et al. (10 pages); Final Office Action mailed Apr. 27, 2007, for related U.S. Appl. No. 10/793,693, Inventor Harold F. Carrison et al. (13 pages); Amendment Response for Final Office Action mailed Apr. 27, 2007, submitted on Aug. 22, 2007, for related U.S. Appl. No. 10/793,693, Inventor Harold F. Carrison et al. (12 pages); Non final Office action mailed Oct. 29, 2007, for related U.S. Appl. No. 10/793,693, Inventor Harold F. Carrison et al. (10 pages); Amendment Response for Final Office Action mailed Oct. 29, 2007, submitted on Feb. 28, 2008, for related U.S. Appl. No. 10/793,693, Inventor Harold F. Carrison et al. (9 pages); and Non final Office action mailed Jul. 9, 2008, for related U.S. Appl. No. 10/793,693, Inventor Harold F. Carrison et al. (10 pages).

(Continued)

*Primary Examiner* — Julie A Szpira
(74) *Attorney, Agent, or Firm* — Bookoff McAndrews, PLLC

(57) ABSTRACT

A tissue removal kit or assembly comprises a cannula and a tissue removal probe axially slidable within the cannula. The tissue removal probe comprises an elongated member a distal end configured to curve when distally deployed from (Continued)

the cannula. The tissue removal probe further comprises a drive shaft rotatably disposed within the member, and a rotatable tissue removal element (e.g., an abrasive burr) disposed on the drive shaft adjacent the member distal end. The curved member distal end may associate the tissue removal element, which has its own axis of rotation, with a radius of revolution about the longitudinal axis of the member. The member is laterally flexible and resilient, so that the radius of revolution can be adjusted. In this manner, the tissue removal element can remove tissue around an adjustable arc.

9 Claims, 19 Drawing Sheets

(51) Int. Cl.
    *A61B 17/32* (2006.01)
    *A61B 17/3207* (2006.01)
    *A61B 17/00* (2006.01)
    *A61B 17/22* (2006.01)
    *A61B 17/29* (2006.01)

(52) U.S. Cl.
    CPC ............... *A61B 17/320758* (2013.01); *A61B 2017/00867* (2013.01); *A61B 2017/2212* (2013.01); *A61B 2017/2215* (2013.01); *A61B 2017/22034* (2013.01); *A61B 2017/2905* (2013.01); *A61B 2017/2927* (2013.01); *A61B 2017/320004* (2013.01); *A61B 2017/320775* (2013.01)

(58) Field of Classification Search
    USPC .................. 606/167, 159, 200; 623/1.11
    See application file for complete search history.

(56) References Cited

U.S. PATENT DOCUMENTS

| | | | |
|---|---|---|---|
| 4,850,957 A | 7/1989 | Summers | |
| 4,983,179 A | 1/1991 | Sjostrom | |
| 5,007,917 A | 4/1991 | Evans | |
| 5,019,088 A | 5/1991 | Farr | |
| 5,030,201 A | 7/1991 | Palestrant | |
| 5,242,418 A | 9/1993 | Weinstein | |
| 5,242,441 A | 9/1993 | Avitall | |
| 5,269,785 A | 12/1993 | Bonutti | |
| 5,312,427 A * | 5/1994 | Shturman | 606/159 |
| 5,356,418 A | 10/1994 | Shturman | |
| 5,360,432 A | 11/1994 | Shturman | |
| 5,376,100 A | 12/1994 | Lefebvre | |
| 5,441,510 A | 8/1995 | Simpson et al. | |
| 5,487,757 A * | 1/1996 | Truckai et al. | 604/264 |
| 5,554,163 A * | 9/1996 | Shturman | 606/159 |
| 5,630,823 A | 5/1997 | Schmitz-Rode et al. | |
| 5,836,947 A | 11/1998 | Fleischman et al. | |
| 5,843,103 A * | 12/1998 | Wulfman | 606/159 |
| 5,849,023 A | 12/1998 | Mericle | |
| 5,857,995 A | 1/1999 | Thomas et al. | |
| 5,913,867 A | 6/1999 | Dion | |
| 5,925,056 A | 7/1999 | Thomas et al. | |
| 5,968,062 A | 10/1999 | Thomas et al. | |
| 6,120,515 A | 9/2000 | Rogers et al. | |
| 6,156,040 A | 12/2000 | Yonemura et al. | |
| 6,228,022 B1 | 5/2001 | Friesem et al. | |
| 6,251,120 B1 | 6/2001 | Dorn | |
| 6,270,498 B1 | 8/2001 | Michelson | |
| 6,280,447 B1 | 8/2001 | Marino et al. | |
| 6,527,065 B1 | 3/2003 | Tibbitts et al. | |
| 6,540,741 B1 | 4/2003 | Underwood et al. | |
| 6,575,981 B1 | 6/2003 | Boyd et al. | |
| 6,582,437 B2 | 6/2003 | Dorchak et al. | |
| 6,596,005 B1 * | 7/2003 | Kanz et al. | 606/159 |
| 6,599,291 B1 | 7/2003 | Foley et al. | |
| 6,610,065 B1 | 8/2003 | Branch et al. | |
| 6,648,895 B2 | 11/2003 | Burkus et al. | |
| 6,740,090 B1 | 5/2004 | Cragg et al. | |
| 6,746,451 B2 | 6/2004 | Middleton et al. | |
| 6,752,767 B2 * | 6/2004 | Turovskiy et al. | 600/564 |
| 6,818,001 B2 | 11/2004 | Wulfman et al. | |
| 6,893,450 B2 * | 5/2005 | Foster | 606/200 |
| 7,077,845 B2 * | 7/2006 | Hacker et al. | 606/80 |
| 7,316,697 B2 | 1/2008 | Shiber | |
| 7,318,826 B2 | 1/2008 | Teitelbaum et al. | |
| 2003/0055404 A1 | 3/2003 | Moutafis | |
| 2004/0147934 A1 | 7/2004 | Kiester | |
| 2005/0054972 A1 | 3/2005 | Adams et al. | |
| 2005/0165420 A1 | 7/2005 | Cha | |
| 2005/0197661 A1 | 9/2005 | Carrison et al. | |
| 2005/0203527 A1 | 9/2005 | Carrison et al. | |
| 2005/0209622 A1 | 9/2005 | Carrison | |
| 2005/0261692 A1 | 11/2005 | Carrison et al. | |
| 2006/0004369 A1 | 1/2006 | Patel et al. | |
| 2007/0010826 A1 | 1/2007 | Rhoda et al. | |
| 2008/0045881 A1 * | 2/2008 | Teitelbaum et al. | 604/21 |

OTHER PUBLICATIONS

Patent Prosecution File History for Related U.S. Appl. No. 10/872,097, filed Jun. 17, 2004, including: Non final Office action mailed May 19, 2006, for related U.S. Appl. No. 10/872,097, Inventor Mukund Patel et al. (6 pages); Amendment Response for Non final Office action mailed May 19, 2006, sumitted on Sep. 19, 2006, for related U.S. Appl. No. 10/872,097, Inventor Mukund Patel et al. (11 pages); Final Office Action mailed Dec. 12, 2006, for related U.S. Appl. No. 10/872,097, Inventor Mukund Patel et al. (7 pages); Amendment Response for final Office action mailed Dec. 12, 2006, submitted on Feb. 26, 2007, for related U.S. Appl. No. 10/872,097, Inventor Mukund Patel et al. (13 pages); Non final Office action mailed May 18, 2007, for related U.S. Appl. No. 10/872,097, Inventor Mukund Patel et al. (6 pages); Amendment Response for final Office action mailed May 18, 2007, submitted on Aug. 17, 2007, for related U.S. Appl. No. 10/872,097, Inventor Mukund Patel et al. (10 pages); Final Office Action mailed Nov. 14, 2007, for related U.S. Appl. No. 10/872,097, Inventor Mukund Patel et al. (8 pages); Amendment Response for Final Office action mailed Nov. 14, 2007, submitted on Feb. 12, 2008, for related U.S. Appl. No. 10/872,097, Inventor Mukund Patel et al. (9 pages); Non final Office action mailed Mar. 25, 2008, for related U.S. Appl. No. 10/872,097, Inventor Mukund Patel et al. (6 pages); and Amendment Response for non final Office action mailed Mar. 25, 2008, submitted on Jul. 16, 2008, for related U.S. Appl. No. 10/872,097, Inventor Mukund Patel et al. (10 pages).

File History for related U.S. Appl. No. 10/793,690, filed Mar. 3, 2004, including: Non Final Office Action mailed Oct. 29, 2007, Inventor Harold F. Carrison et al. (6 pages).

File History for related U.S. Appl. No. 10/793,185, filed Mar. 3, 2004 including: Non Final Office Action mailed May 16, 2007, Inventor Harold F. Carrison et al. (6 pages); and Response to Non Final office action mailed May 16, 2007, submitted on Aug. 16, 2007, Inventor Harold F. Carrison (7 pages).

Papers from file history for related U.S. Appl. No. 10/793,693, filed Mar. 3, 2004, Inventor Harold F. Carrison, et al., including (8 pages total): Pre-Appeal Brief Conference Decision for U.S. Appl. No. 10/793,693, dated Apr. 27, 2009; and Pre-Appeal Brief Request for Review for U.S. Appl. No. 10/793,693, submitted Mar. 25, 2009.

Papers from file history for related U.S. Appl. No. 10/793,185, filed Mar. 3, 2004, Inventor Harold F. Carrison, et al., including (18 pages total): Amendment and Response to non final rejection mailed May 18, 2009, for U.S. Appl. No. 10/793,185, submitted Aug. 18, 2009; and Non final rejection for U.S. Appl. No. 10/793,185, mailed May 18, 2009.

File History for related U.S. Appl. No. 10/793,693, filed Mar. 3, 2004, including: Final Office Action dated Jan. 9, 2009 for related

(56) References Cited

OTHER PUBLICATIONS

U.S. Appl. No. 10/793,693, filed Mar. 3, 2004, inventor Harold F. Carrison (13 pages); and Amendment and Response to Non-Final Office Action dated Jul. 9, 2008, submitted on Oct. 6, 2008 for related U.S. Appl. No. 10/793,693, filed Mar. 3, 2004, inventor Harold F. Carrison (10 pages).

File History for related U.S. Appl. No. 10/793,185, filed Mar. 3, 2004, including: Amendment and Response to Final Office Action dated Oct. 28, 2008, submitted on Jan. 28, 2009 for related U.S. Appl. No. 10/793,185, filed Mar. 3, 2004, inventor Harrison F. Carrison (9 pages); and Final Office Action dated Oct. 28, 2008 for related U.S. Appl. No. 10/793,185, filed Mar. 3, 2004, inventor Harold F. Carrison (9 pages).

File History for related U.S. Appl. No. 10/872,097, filed Jun. 17, 2004, including: Pre Brief Conference Request for Review, submitted on Jan. 28, 2009, for related U.S. Appl. No. 10/872,097, Inventor Mukund Patel et al. (5 pages); and Final office action mailed Oct. 28, 2008 for related U.S. Appl. No. 10/872,097, Inventor Mukund Patel et al. (7 pages).

* cited by examiner

RADIALLY ADJUSTABLE TISSUE REMOVAL DEVICE

RELATED APPLICATIONS

This application is a continuation of pending application U.S. Ser. No. 10/793,694, filed Mar. 3, 2004, which is related to application Ser. Nos. 10/793,185 and 10/793,690, both filed Mar. 3, 2004, now abandoned, all of which are expressly incorporated herein by reference.

FIELD OF THE INVENTION

The field of the invention pertains to medical devices and methods for removing tissue, and in particular, vertebral bone and intervertebral disc tissue.

BACKGROUND OF THE INVENTION

The spinal column consists of thirty-three bones called vertebra, the first twenty-four vertebrae of which make up the cervical, thoracic, and lumbar regions of the spine and are separated from each other by "pads" of tough cartilage called "intervertebral discs," which act as shock absorbers that provide flexibility, stability, and pain-free movement of the spine.

FIGS. 1 and 2 illustrate a portion of a healthy and normal spine, and specifically, two vertebra 10 and two intervertebral discs 12 (only one shown). The posterior of the vertebra 10 includes right and left transverse processes 14R, 14L, right and left superior articular processes 16R, 16L, and a spinous process 18. Muscles and ligaments that move and stabilize the vertebra 10 are connected to these structures. The vertebra 10 further includes a centrally located lamina 20 with right and left lamina 20R, 20L, that lie inbetween the spinous process 18 and the superior articular processes 16R, 16L. Right and left pedicles 22R, 22L are positioned anterior to the right and left transverse processes 14R, 14L, respectively. A vertebral arch 24 extends between the pedicles 22 and through the lamina 20. The anterior of the vertebra 10 includes a vertebral body 26, which joins the vertebral arch 24 at the pedicles 22. The vertebral body 26 includes an interior volume of reticulated, cancellous bone (not shown) enclosed by a compact cortical bone 30 around the exterior. The vertebral arch 24 and vertebral body 26 make up the spinal canal (i.e., the vertebral foramen 32), which is the opening through which the spinal cord 34 and epidural veins (not shown) pass. Nerve roots 36 laterally pass from the spinal cord 34 out through the neural foramen 38 at the side of the spinal canal formed between the pedicles 22. Structurally, the intervertebral disc 12 consists of two parts: an inner gel-like nucleus (nucleus pulposus) 40 located centrally within the disc 12, and tough fibrous outer annulus (annulus fibrosis) 42 surrounding the nucleus 40.

A person may develop any one of a variety of debilitating spinal conditions and diseases. For example, as illustrated in FIG. 3, when the outer wall of the disc 12' (i.e., the annulus fibrosis 42) becomes weakened through age or injury, it may tear allowing the soft inner part of the disc 12 (i.e., the nucleus pulposus 40) to bulge out, forming a herniation 46. The herniated disc 12' often pinches or compresses the adjacent dorsal root 36 against a portion of the vertebra 10, resulting in weakness, tingling, numbness, or pain in the back, legs or arm areas.

Often, inflammation from disc herniation can be treated successfully by nonsurgical means, such as bedrest, therapeutic exercise, oral anti-inflammatory medications or epidural injection of corticosterioids, and anesthetics. In some cases, however, the disc tissue is irreparably damaged, in which case, surgery is the best option.

Discectomy, which involves removing all, or a portion, of the affected disc, is the most common surgical treatment for ruptured or herniated discs of the lumbar spine. In most cases, a laminotomy or laminectomy is performed to visualize and access the affected disc. Once the vertebrae, disc, and other surrounding structures can be visualized, the surgeon will remove the section of the disc that is protruding from the disc wall and any other offending disc fragments that may have been expelled from the disc. In some cases, the entire disc may be removed, with or without a bony fusion or arthroplasty (disc nucleus replacement or total disc replacement).

Open discectomy is usually performed under general anesthesia and typically requires at least a one-day hospital stay. During this procedure, a two to three-inch incision in the skin over the affected area of the spine is made. Muscle tissue may be separated from the bone above and below the affected disc, while retractors hold the wound open so that the surgeon has a clear view of the vertebrae and disc and related structures. The disc or a portion thereof, can then be removed using standard medical equipment, such as rongeurs and curettes.

Because open discectomy requires larger incisions, muscle stripping or splitting, more anesthesia, and more operating, hospitalization, and a longer patient recovery time, the trend in spine surgery is moving towards minimally invasive surgical techniques, such as microdiscectomy and percutaneous discectomy.

Microdiscectomy uses a microscope or magnifying instrument to view the disc. The magnified view may make it possible for the surgeon to remove herniated disc material through a smaller incision (about twice as small as that required by open discectomy) with smaller instruments, potentially reducing damage to tissue that is intended to be preserved.

Percutaneous discectomy is often an outpatient procedure that may be carried out by utilizing hollow needles or cannulae through which special instruments can be deployed into the vertebra and disc in order to cut, remove, irrigate, and aspirate tissue. X-ray pictures and a video screen and computer-aided workstation may be used to guide by the surgeon into the treatment region. Improved imaging and video or computer guidance systems have the potential to reduce the amount of tissue removal required to access and treat the injured tissue or structures. Sometimes an endoscope is inserted to view the intradiscal and perivertebral area.

Besides disc hernias, other debilitating spinal conditions or diseases may occur. For example, spinal stenosis, which results from hypertrophic bone and soft tissue growth on a vertebra, reduces the space within the spinal canal. When the nerve roots are pinched, a painful, burning, tingling, and/or numbing sensation is felt down the lower back, down legs, and sometimes in the feet. As illustrated in FIG. 2, the spinal canal 32 has a rounded triangular shape that holds the spinal cord 34 without pinching. The nerve roots 36 leave the spinal canal 32 through the nerve root canals 38, which should be free of obstruction. As shown in FIG. 4, hypertrophic bone growth 48 (e.g., bone spurs, osteophytes, spondylophytes) within the spinal canal 32, and specifically from the diseased lamina 20 and proximate facet joints may cause compression of the nerve roots, which may contribute or lead to the pain of spinal stenosis. Spinal stenosis may be treated by performing a laminectomy or laminectomy in order to decompress the nerve root 36 impinged by the bone growth 48. Along with the laminectomy, a foraminotomy, (i.e., enlarging of the channel from which the nerve roots 36 exit is performed). Depending on the extent of the bone growth, the entire lamina and spinal process may be removed.

Another debilitating bone condition is a vertebral body compression fracture (VCF), which may be caused by spinal injuries, bone diseases such as osteoporosis, vertebral hemangiomas, multiple myeloma, necorotic lesions (Kummel's Disease, Avascular Necrosis), and metastatic disease, or other conditions that can cause painful collapse of vertebral bodies. VCFs are common in patients who suffer from these medical conditions, often resulting in pain, compromises to activities of daily living, and even prolonged disability.

On some occasions, VCFs may be repaired by cutting, shaping, and removing damaged bone tissue inside a vertebra to create a void, and then injecting a bone cement percutaneously or packing bone graft into the void. This is typically accomplished percutaneously through a cannula to minimize tissue trauma. The hardening (polymerization) of a bone cement media or bone grafting or other suitable biomaterial serves to buttress the bony vault of the vertebral body, providing both increased structural integrity and decreased pain that may be associated with micromotion and progressive collapse of the vertebrae.

Thus, it can be appreciated that in many spinal treatment procedures, bone and/or disc tissue must be removed in order to decompress neural tissue or rebuild the bony vertebra or intervertebral disc. In the case of target bone tissue that is adjacent spinal tissue, a physician is required to exercise extreme care when cutting away the target bone tissue (e.g., during a laminectomy and foraminotomy), such that injury to spinal tissue can be prevented. A physician may have difficulty controlling existing bone removal devices, however, and may unintentionally remove healthy bone tissue or injure spinal tissue during use. This problem is exacerbated with percutaneous treatments, which, although less invasive than other procedures, limit the range of motion of the cutting instrument, thereby further limiting the control that the physician may have during the bone cutting procedure.

Burr-type tissue removal probes may also be used to remove soft tissue, such as the gel-like nuclear tissue within the intervertebral disc or the cancellous bone tissue within the vertebral body. For example, FIG. 5 illustrates one prior art burr-type tissue removal probe 50 that can be introduced through a delivery cannula (not shown) into contact with the target tissue region to be removed. The tissue removal probe 50 comprises a rigid shaft 52 and a rotatable burr 54 associated with the distal end of the rigid shaft 52. Rotation of a drive shaft 56 extending through the rigid shaft 52, in turn, causes rotation of the burr 54 (either manually or via a motor), thereby removing tissue that comes in contact with the burr 54. Notably, the tissue removal probe 50 is laterally constrained within the cannula (or if a cannula is not shown, constrained by the many layers of tissue that the device 50 must traverse to reach the target tissue), and thus, can only be effectively moved along its longitudinal axis, thereby limiting the amount of tissue that can be removed to the tissue that is on-axis. As such, the tissue removal probe 50 may have to be introduced through several access points within the anatomical body (e.g., the disc or vertebral body) that contains the target tissue in order to remove the desired amount of the tissue.

As illustrated in FIG. 6, the distal end 58 of the rigid shaft 52 may be curved in an alternative prior art removal device 60, so that the burr 54 is off-axis from the shaft 52. As such, off-axis target regions can be reached by rotating and axially displacing the rigid shaft 52 about its axis. Because the length of the curved distal end is fixed, however, only the tissue regions that are off-axis by a distance equal to the off-axis distance of the burr 54 will be removed, as illustrated in FIG. 7. In effect, the removal device 60 can only remove a cylindrical outline 62 of the tissue, leaving a cylindrical tissue body 64 behind. Thus, the tissue removal probe 60 must still be introduced into the tissue via several access holes in order to remove any remaining tissue.

In addition, because the distal end of the rigid shaft 52 is curved and has a length of the distal tip that is now at an angle to the main shaft, the delivery cannula must be made larger to accommodate the entire profile of the distal end. Thus, the incision through which the cannula is introduced must likewise be made larger. Lastly, if the anatomical body in which the removal device 60 is introduced is relatively thin (e.g., an intervertebral disc is a few millimeters thick), the top or bottom of the anatomical body may hinder movement of the burr 54 as the shaft 52 is rotated around its axis. In such cases, the removal device 60 may have to be introduced along the bottom of the anatomical body to allow tissue to be removed at the top of the anatomical body (i.e., by sweeping the burr 54 along an upper arc until the burr 54 hits the top, or if clearance at the top is available, by sweeping the burr 54 along the upper arc, below the top, until the burr 54 hits the bottom), and then reintroduced along the top of the anatomical body to allow tissue to be removed at the bottom of the anatomical body (i.e., by sweeping the burr 54 along a lower arc until the burr 54 hits the bottom, or if clearance at the bottom is available, by sweeping the burr 54 along the lower arc, above the bottom, until the burr 54 hits the top). As can be appreciated, this excessive movement of the removal device 60 increases the time of the spinal procedure as well as surgical risk due to manipulation of the device.

Another problem with current burr-type removal devices is that soft material, such as the nuclear material in an intervertebral disc or cancellous bone within the vertebral body, tends to stick to the burrs, thereby limiting the abrasive effect that the burrs are intended to have in order to efficiently remove tissue. As a result, burr-type removal device may have to be continuously removed from the patient's body in order to clean the soft tissue from the burr.

Furthermore, during the tissue removal or cutting process, a media, such as saline, is generally delivered via a tube to a target site for clearing debris. The delivered media together with the debris are then removed from the target site via a separate tube (i.e., the media and the debris are aspirated into a vacuum port of the tube). When the spine is treated percutaneously, however, the delivery cannula must be made large enough to accommodate the tissue removal probe and tubes. As a result, the incision through which the cannula is to be introduced must be made relatively large, thereby unnecessarily causing more tissue trauma.

There, thus, remains a need to provide for improved tissue removal probes and methods for use during spinal treatment and other surgeries.

SUMMARY OF THE INVENTION

In accordance with a first aspect of the present invention, a tissue removal probe is provided. The tissue removal probe particularly lends itself to the removal of soft tissue, such as that contained in intervertebral discs and the cancellous bone in vertebral bodies, but can be used to remove other types of tissue as well. The tissue removal probe comprises an elongated member (such as a sleeve) having a lumen and a pre-curved flexible distal end, a drive shaft rotatably disposed within the member lumen, and a rotatably tissue removal element (e.g., an abrasive burr) disposed on the drive shaft adjacent the member distal end. In one embodiment, the member distal end can be pre-curved at approximately ninety degrees, although other curvatures are possible. By way of non-limiting example, the pre-curved member distal end may associate the tissue removal element, which has its own axis of rotation, with a radius of revolution about the longitudinal axis of the member. The member is laterally flexible and resilient, so that the radius of revolution can be adjusted. The probe may optionally comprise a proximal adapter mounted to the member for mating with a drive unit.

In accordance with a second aspect of the present invention, the tissue removal kit comprises a cannula, which may be rigid, e.g., so that it can be introduced through tissue without the aid of other instruments. The cannula may have a tissue-penetrating distal tip to facilitate its introduction harder tissue, such as bone tissue. The tissue removal kit further comprises a tissue removal probe axially slidable within the cannula lumen. The tissue removal probe may optionally be removable from the cannula lumen, so that the cannula can be used for other functions, e.g., delivering therapeutic media. The tissue removal probe comprises an elongated member having a lumen and a distal end configured to curve when distally deployed from the cannula lumen. The deployed member distal end can be configured to curve in any one of a variety of manners. For example, the distal end of the cannula may be curved, the member distal end may be pre-curved, or pull wire(s) can be provided to actively bend the member distal end. In one embodiment, the member distal end can be curved at approximately ninety degrees, although other curvatures are possible.

The tissue removal probe further comprises a drive shaft rotatably disposed within the member lumen, and a rotatable tissue removal element (e.g., an abrasive burr) disposed on the drive shaft adjacent the member distal end. By way of non-limiting example, the curved member distal end may associate the tissue removal element, which has its own axis of rotation, with a radius of revolution about the longitudinal axis of the straight portion of the member. The member is laterally flexible and resilient, so that the radius of revolution can be adjusted. The probe may optionally comprise a proximal adapter mounted to the member for mating with a drive unit.

In accordance with a third aspect of the present inventions, a method of removing tissue from an anatomical body (e.g., an intervertebral disc or vertebral body) is provided. The method comprises introducing a cannula into the anatomical body at a first location, and introducing a tissue removal probe through the cannula. The tissue removal probe may be introduced into the cannula prior or subsequent to the introduction of the cannula into the anatomical body. The tissue removal probe comprises an elongated member having a straight portion and a distal end, and a distally located tissue removal element associated with the member distal end. The method further comprises displacing the tissue removal element a first distance from the cannula, wherein the distal end bends to associate the tissue removal element with a first radius of revolution about a rotational axis of the straight portion of the member. In one method, the member distal end bends because it is pre-curved or the cannula distal end is curved. The method further comprises rotating the member around its rotational axis, wherein the tissue removal element scribes a first arc defined by the first radius of revolution. In one preferred method, the first arc forms an entire circle. The method further comprises rotating the tissue removal element about its axis of rotation to remove tissue at at least two points along the first arc. The tissue removal element may be rotated while the straight member portion is rotated, so that the tissue removal element continuously removes tissue along the first arc.

Optionally, the method may comprise displacing the tissue removal element a second distance from the cannula, wherein the distal end bends to associate the tissue removal element with a second radius of revolution different from the first radius of revolution. The method may further comprise rotating the straight member portion around the first axis of rotation, wherein the tissue removal element scribes a second arc defined by the second radius of revolution (which may be greater than the first radius of revolution), and rotating the tissue removal element about the second axis of rotation to remove tissue at at least two points along the second arc. The second arc may also form an entire circle. In this case, a solid disc of tissue may be removed.

The method may optionally comprise displacing the cannula along the first axis of rotation to a second location, and repeating the member distal end displacement, straight member portion rotation, and tissue removal element rotation steps. In this case, a solid cylinder of tissue is removed if the first and second arcs are entire circles.

In accordance with a fourth aspect of the present inventions, another method of removing tissue from an anatomical body (e.g., an intervertebral disc or vertebral body) is provided. The method comprises introducing a cannula into the anatomical body at a first location, and introducing a tissue removal probe through the cannula. The tissue removal probe may be introduced into the cannula prior or subsequent to the introduction of the cannula into the anatomical body.

The tissue removal probe comprises an elongated member having a distal end, and a distally located tissue removal element associated with the member distal end. The method further comprises displacing the tissue removal element a first distance from the cannula to associate the tissue removal element with a first radius of curvature. The method further comprises bending the member distal end, wherein the tissue removal element scribes a first arc defined by the first radius of curvature. In one method, the member distal end can be actively bent using at least one pull wire. In one preferred method, the first arc forms a semi-circle. The method further comprises rotating the tissue removal element about its axis of rotation to remove tissue at at least two points along the first arc. The tissue removal element may be rotated while the member distal end is bent, so that the tissue removal element continuously removes tissue along the first arc.

Optionally, the method may comprise displacing the tissue removal element a second distance from the cannula to associate the tissue removal element with a second radius of curvature different from the first radius of curvature. The method may further comprise bending the member distal end, wherein the tissue removal element scribes a second arc defined by the second radius of curvature (which may be greater than the first radius of curvature), and rotating the tissue removal element about its axis of rotation to remove tissue at at least two points along the second arc. The second arc may also form a semi-circle. In this case, a solid sector of tissue may be removed.

BRIEF DESCRIPTION OF THE DRAWINGS

The drawings illustrate the design and utility of preferred embodiments of the present invention. It should be noted that the figures are not drawn to scale and that elements of similar structures or functions are represented by like reference numerals throughout the figures. In order to better appreciate how the above-recited and other advantages and objects of the present inventions are obtained, a more particular description of the present inventions briefly described above will be rendered by reference to specific embodiments thereof, which are illustrated in the accompanying drawings. Understanding that these drawings depict only typical embodiments of the invention and are not therefore to be considered limiting of its scope, the invention will be described and explained with additional specificity and detail through the use of the accompanying drawings in which.

DETAILED DESCRIPTION OF THE EMBODIMENTS

Figure 1:
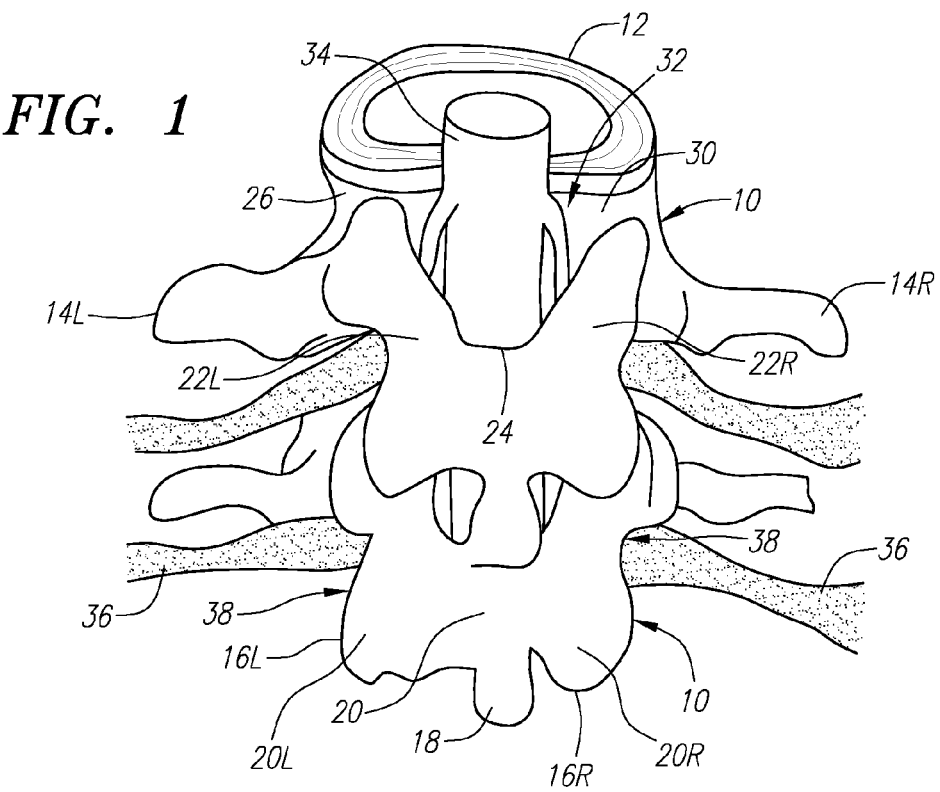
FIG. 1 is a perspective view of a portion of a spine.
Figure 2:
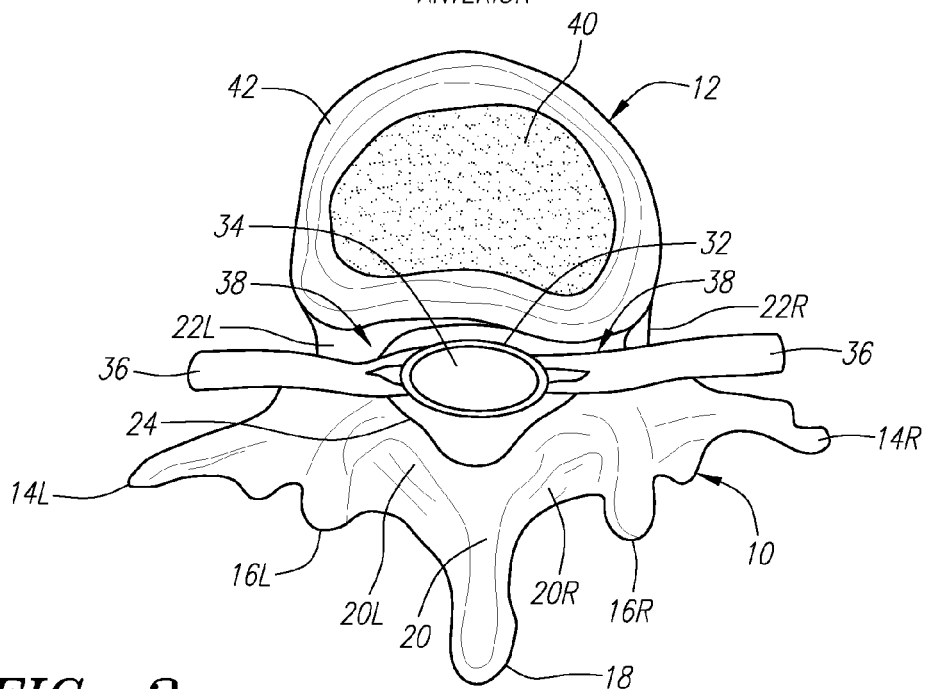
FIG. 2 is a top view of a vertebra with a healthy intervertebral disc.
Figure 3:
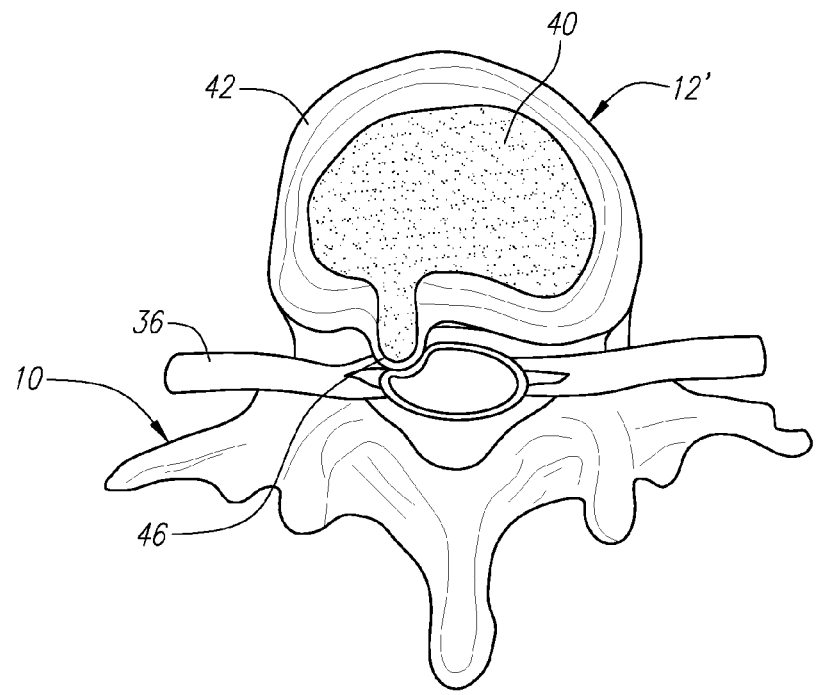
FIG. 3 is a top view of a vertebra with a herniated intervertebral disc.
Figure 4:
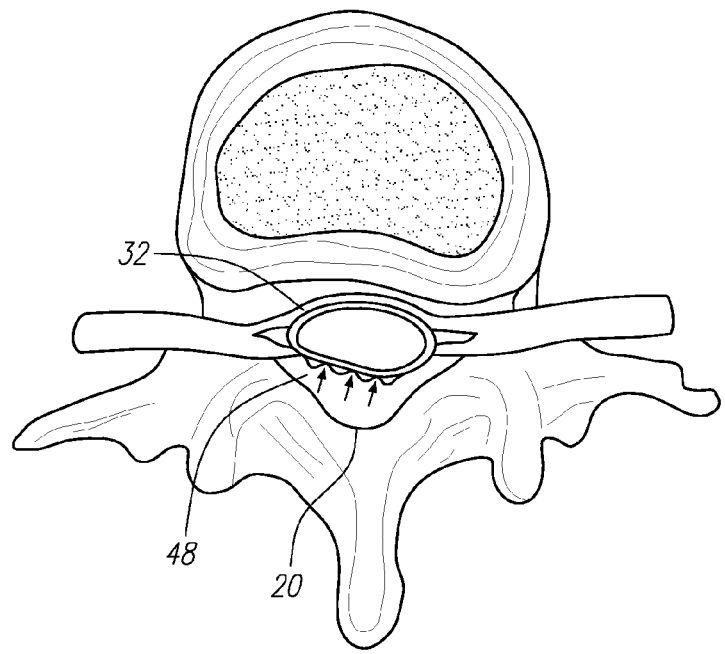
FIG. 4 is a top view of a vertebra with spinal stenosis.
Figure 5:
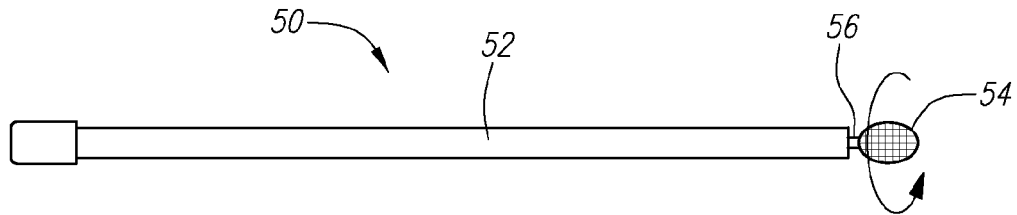
FIG. 5 is a prior art tissue removal probe.
Figure 6:
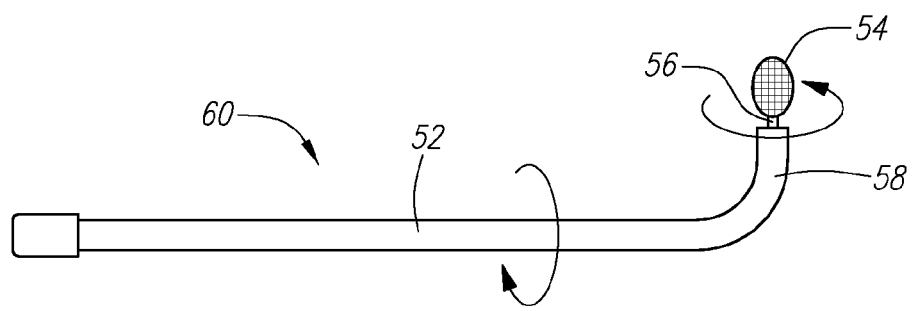
FIG. 6 is another prior art tissue removal probe.
Figure 7:
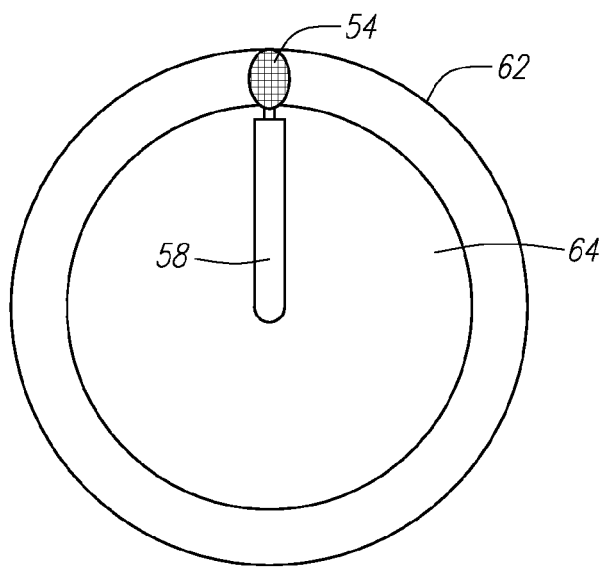
FIG. 7 is a plan view showing tissue removal using the tissue removal probe of FIG. 6.
Figure 8:
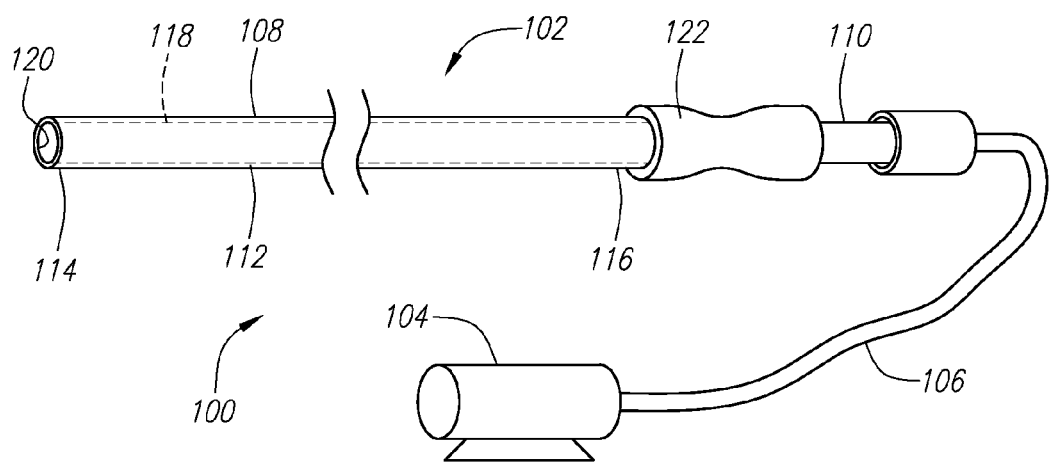
FIG. 8 is a perspective view of a tissue removal system arranged in accordance with a preferred embodiment of the present invention.

FIG. 8 illustrates a tissue removal system 100 constructed in accordance with a preferred embodiment of the present inventions. The system 100 generally comprises a tissue removal probe assembly 102 and a rotary drive unit 104 connected to the probe assembly 102 via a drive cable 106. The drive unit 104 may take the form of a standard rotary drive used for powering medical cutting instruments. The tissue removal probe assembly 102 comprises a cannula 108 and a tissue removal probe 110 disposed therein.

The cannula 108 comprises a shaft 112 having a distal end 114 and proximal end 116, a lumen 118 (shown in phantom) terminating in an exit port 120 at the distal end 114 of the cannula shaft 112, and a handle 122 mounted on the proximal end 116 of the cannula shaft 112. To facilitate introduction through tissue, the cannula shaft 112 is preferably stiff (e.g., it can be composed of a stiff material, or reinforced with a coating or a coil to control the amount of flexing), so that the cannula shaft 112 can penetrate the tissue without being damaged. The materials used in constructing the cannula shaft 112 may comprise any of a wide variety of biocompatible materials. In a preferred embodiment, a radiopaque material, such as metal (e.g., stainless steel, titanium alloys, or cobalt alloys) or a polymer (e.g., ultra high molecular weight polyethylene) may be used, as is well known in the art. Alternatively, if supported by a rigid member during introduction into the tissue, the cannula shaft 112 may be flexible. The handle 122 is preferably composed of a durable and rigid material, such as medical grade plastic, and is ergonomically molded to allow a physician to more easily manipulate the cannula 108.

The outer diameter of the cannula shaft 112 is preferably less than ½ inch, but other dimensions for the outer diameter of the cannula shaft 112 may also be appropriate, depending on the particular application or clinical procedure. The cannula lumen 118 should have an inner diameter so as to allow the tissue removal probe 110 to be slidably housed therein, as will be described in further detail below. In the illustrated embodiment, the profile of the cannula lumen 118 is circular, but can be other shapes as well. In the illustrated embodiment, the distal tip of the cannula shaft 112 is blunt. In this case, the thickness and cross-sectional profile of the cannula shaft 112 is small enough, so that the distal tip can be used as a cutting or deforming tool for boring or coring through tissue. Alternatively, the distal tip of the cannula shaft 112 may be advantageously sharpened or wedged to facilitate its introduction into bone structure. Even more alternatively, a stilette (not shown) can be introduced through the cannula lumen 118 to provide an independent means for boring through bone structure. In this manner, bone cores will not block the cannula lumen 118, which may otherwise prevent, or at least make difficult, deployment of the tissue removal probe 110 and other therapeutic materials.

Figure 9:
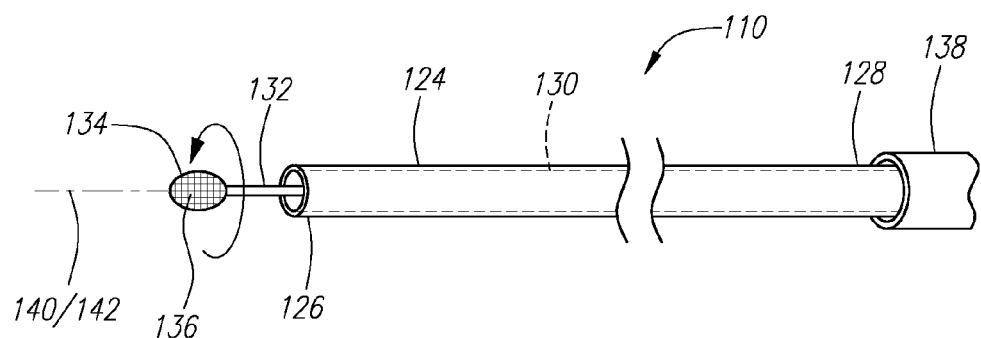
FIG. 9 is perspective view of a tissue removal probe that can be used in the system of FIG. 8.

Referring now to FIG. 9, the tissue removal probe 110 will described in further detail. The tissue removal probe 110 comprises a sleeve 124 having a distal end 126 and a proximal end 128, and a lumen 130 (shown in phantom) extending through the sleeve 124. The tissue removal probe 110 further comprises a drive shaft 132 rotatably disposed within the sleeve lumen 130 and a rotatable tissue removal element, and in particular, an abrasive burr 134, mounted to the distal end of the drive shaft 132. The burr 134 has a pattern of cutting edges 136 that facilitate removal of tissue that comes in contact with the rotating burr 134. In the illustrated embodiment, the burr 134 is fully exposed in that it entirely resides outside of the sleeve 124. In alternative embodiments, the burr 134 may be seated within the distal end of a sheath, and exposed through a window cutout from the distal end of the sheath. Other types of tissue-cutting element can also be used in place of the burr 134. Examples of other tissue-cutting elements will subsequently be described.

The tissue removal probe 110 further comprises a proximal adapter 138 mounted to the proximal end 128 of the sleeve 124. The proximal adapter 138 is configured to be mated with the drive cable 106, thereby providing a means for rotatably coupling the drive unit 104 to the proximal end of the drive shaft 132. Thus, operation of the drive unit 104 will rotate the drive shaft 132, which in turn, will rotate the burr 134 about its rotational axis 140. Details of the structure of standard tissue removal probes, including the aforementioned window-exposed burr and proximal adapter, are disclosed in U.S. Pat. No. 5,913,867, which is expressly incorporated herein by reference.

The tissue removal probe 110 is rotatably disposed within the cannula lumen 118, such that the sleeve 124 (and in particular, the straight portion of the sleeve) has an axis of rotation 142 (i.e., the sleeve 124 can be rotated about the rotational axis 142, e.g., when the proximal end 128 of sleeve distal end 126 is manually rotated). As illustrated in FIG. 9, the rotational axes 140 and 142 of the respective burr 132 and sleeve 124 are coincident with each other when the entirety of the sleeve 124 is straight. As will be described in below, the rotational axes 140 and 142 will diverge from each other when the distal end 126 of the sleeve 124 is curved or bent.

Figure 10:
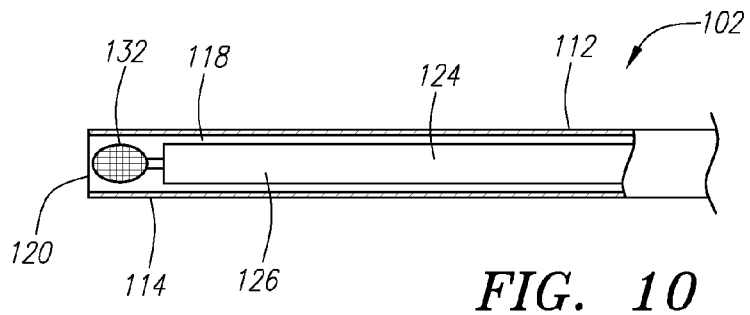
FIG. 10 is a partially cutaway side view of the distal end of the probe of FIG. 9, particularly showing the tissue removal element retracted within the probe shaft.
Figure 11:
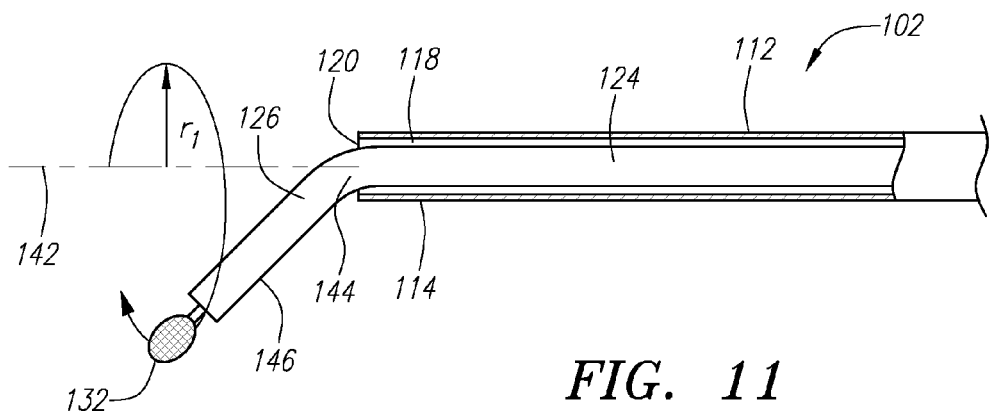
FIG. 11 is a partially cutaway side view of the distal end of the probe of FIG. 9, particularly showing the tissue removal element partially deployed from the probe shaft.
Figure 12:
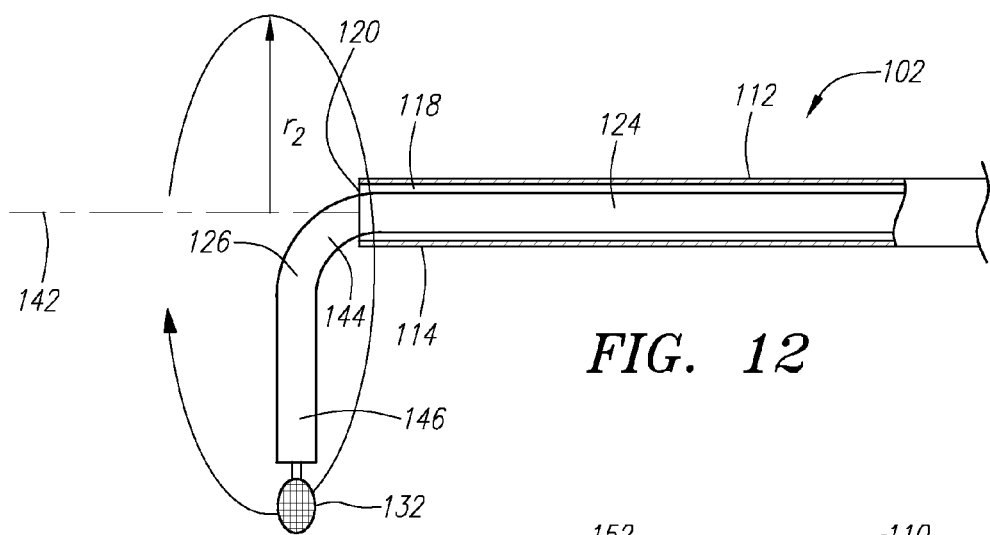
FIG. 12 is a partially cutaway side view of the distal end of the probe of FIG. 9, particularly showing the tissue removal element fully deployed from the probe shaft.

As illustrated in FIGS. 10-12, the tissue removal probe 110 is slidably disposed in the cannula lumen 118 in the longitudinal direction, so that the burr 134 can be incrementally deployed from the exit port 120 of the cannula shaft 112 and retracted within the distal end 114 of the cannula shaft 112.

As can be seen from FIG. 10, when confined within the cannula lumen 118, the sleeve 124 assumes a substantially straight configuration and conforms to the shape of the cannula shaft 112. As can be seen from FIGS. 11 and 12, the distal end 126 of the sleeve 124, when in its relaxed state, has a pre-shaped curved portion 144 and a pre-shaped straight portion 146 distal to the curved portion 144. In the illustrated embodiment, the curved portion 144 defines an arc of ninety-degrees. It should be noted, however, the curved portion 144 may define other arcs. So that the distal end 126 of the sleeve 124 readily assumes and maintains its defined shape, the sleeve 124 is composed of a laterally flexible, yet resilient, material, such as nitinol. Significantly, the drive shaft 132 is also laterally flexible, and thus easily conforms to the curved geometry of the deployed sleeve distal end 126. In this manner, the burr 134 will rotate about its rotational axis 140 even if the drive shaft 132 is bent.

As can be appreciated from FIGS. 11 and 12, the distal end 126 of the sleeve 124 can be deployed from the cannula exit port 120 in stages. For example, the sleeve distal end 126 can be deployed a first distance from the distal end 114 of the cannula shaft 112, so that the burr 134 defines a particular radius of revolution $r_1$ (shown in FIG. 11) around the rotational axis 142 of the sleeve 124. The sleeve distal end 126 can be deployed a second greater distance from the distal end 126 of the cannula shaft 112, so that the burr 134 defines a second greater radius of revolution $r_2$ (shown in FIG. 12) around the rotational axis 142 of the sleeve 124. Thus, it can be appreciated that radius of revolution r of the burr 134 can be adjusted simply by displacing the sleeve 124 within the cannula lumen 118.

Figure 13:
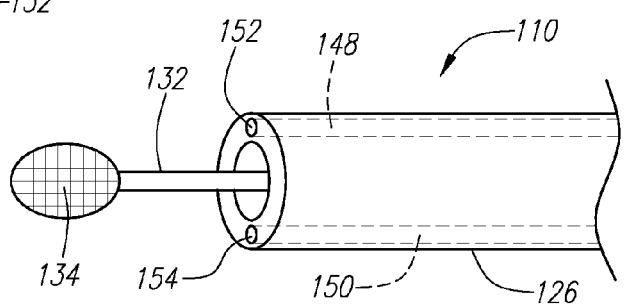
FIG. 13 is a perspective view of a variation of the probe of FIG. 9, particularly showing irrigation and aspiration lumens.

As illustrated in FIG. 13, the tissue removal probe 110 can optionally have irrigation and aspiration capability. In particular, the sleeve 124, in addition to having the lumen 130 through which the drive shaft 132 extends, includes irrigation and aspiration lumens 148 and 150 (shown in phantom). The irrigation lumen 148 terminates at an irrigation outlet port 152 in the sleeve distal end 126 and proximally terminates at an irrigation inlet port (not shown) in the proximal adapter 138. Likewise, the aspiration lumen 150 terminates at an aspiration entry port 154 in the sleeve distal end 126 and proximally terminates at an aspiration outlet port (not shown) in the proximal adapter 138. Alternatively, irrigation and/or aspiration ports can be placed in the burr 134.

As can be appreciated, a pump (not shown) can be connected to the irrigation inlet port on the proximal adapter 138 in order to flush irrigation fluid, such as saline, through the irrigation lumen 148 and out the irrigation outlet port 152. The irrigation fluid helps cool the drive shaft 132 and/or the burr 134, while the burr 134 is rotating at high speed and grinding against tissue. The media also washes away debris at the target site. A vacuum (not shown) can be connected to the aspiration outlet port on the proximal adapter 138 in order to aspirate the removed tissue into the aspiration inlet port 154, through the aspiration lumen 150, and out of the aspiration outlet port. Because there are separate irrigation and aspiration lumens 148 and 150, both the pump and aspirator can be activated simultaneously or separately.

Having described the structure of the tissue removal system 100, its operation will now be described with reference to FIGS. 14A-14G, in removing soft tissue from an anatomical body, and in particular, in performing a discectomy on a herniated intervertebral disc. It should be noted, however, that other tissue, such as the cancellous tissue within a vertebral body, could also be removed by the tissue removal system 100.

Figure 14A:
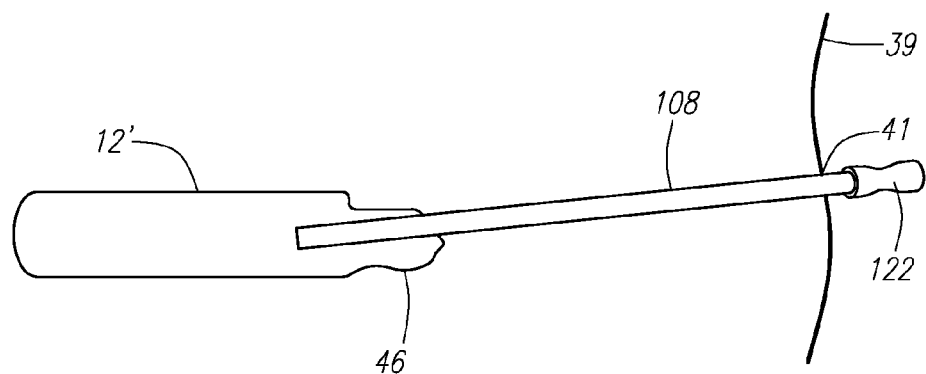
FIGS. 14A-14G are perspective views showing a method of using the tissue removal system of FIG. 8 to remove tissue within a herniated intervertebral disc.
Figure 14B:
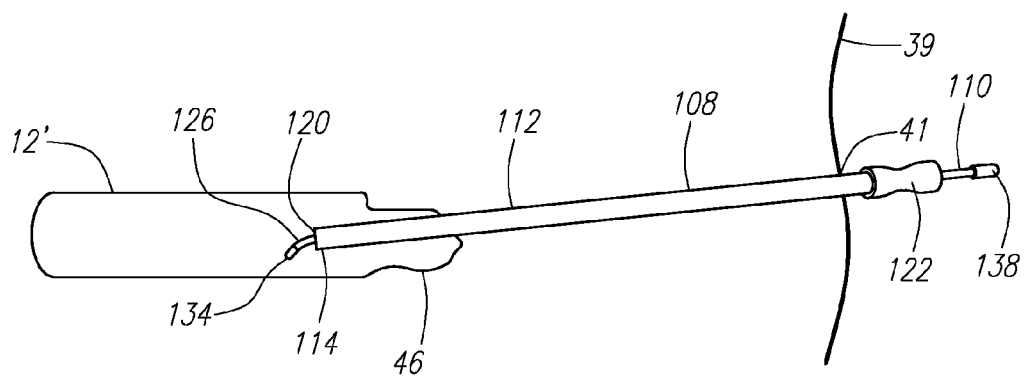

First, the cannula 108 is introduced through a small incision 41 in the back 39 and into the herniated disc 12' (FIG. 14A). In some circumstances, a laminectomy may have to be performed to access the disc 12'. In such cases, the cannula 108 may be used to bore through the lamina (not shown). Torsional and/or axial motion may be applied to the cannula 108 to facilitate boring of the lamina. The torsional and/or axial motion may be applied manually or mechanically (i.e., by a machine). An object, such as a hammer or a plunger, may also be used to tap against the handle 122 of the cannula 108 in order to facilitate boring through the lamina. Alternatively, a stilette (not shown) can be introduced through the cannula lumen (not shown in FIG. 14A) to create a passage through the lamina. Or, a separate drill or bone cutting device, such as those described below, can be used to bore or cut a passage through the lamina prior to placement of the cannula 108.

In the illustrated method, the cannula 108 is introduced into the disc 12', such that its distal tip is placed adjacent the distal-most region of the target tissue. In this case, distal to the herniation 46. Next, the tissue removal probe 110 is introduced through the cannula lumen 118 until the distal end 126 of the sleeve 124 deploys out from exit port 120 of the cannula shaft 112 a first distance (FIG. 14B), which as described above, associates the burr 134 with a first radius of revolution $r_1$ around the rotational axis 142 of the sleeve 124. The tissue removal probe 110 can either be introduced into the cannula lumen 118 prior to introduction of the cannula 108 into the patient's back (in which case, the tissue removal probe 110 will be fully retracted within the cannula lumen 118 during introduction of the cannula 108) or can be introduced into the cannula lumen 118 after the cannula 108 has been introduced into, and properly positioned, within the disc 12'.

Figure 14C:
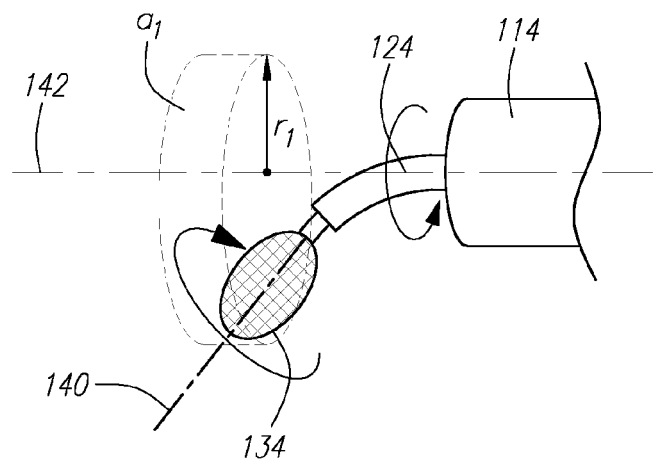
Figure 14D:
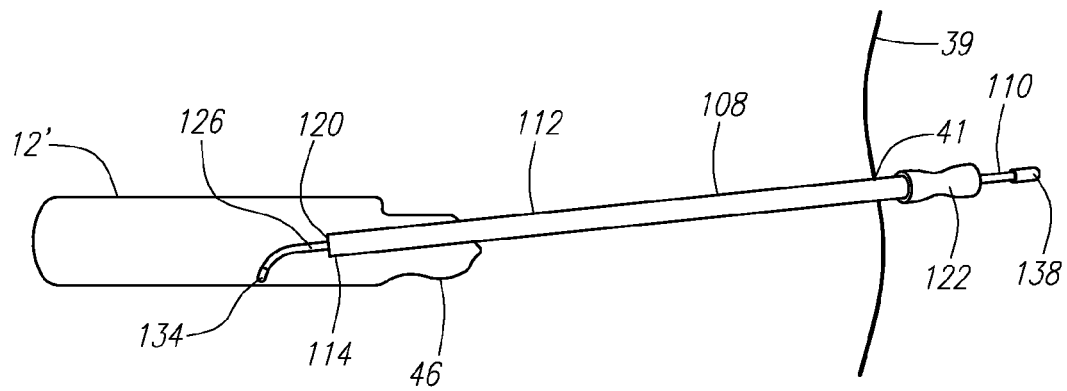

Next, the proximal adapter 138 of the tissue removal probe 110 is mated to the drive unit (shown in FIG. 8), which is then operated to rotate the burr 134 about is own rotational axis 140. At the same time, the sleeve 124 is manually rotated (e.g., by rotating the proximal adapter 138), which causes the burr 134 to scribe an arc $a_1$ around the rotational axis 142 of the sleeve 124 (FIG. 14C). As a result, tissue is removed by the rotating burr 134 along the arc $a_1$. In the illustrated method, the sleeve 124 is rotated until the burr 134 scribes an entire circle around the rotational axis 142 of the sleeve 124. In this manner, a full circle of tissue is removed by the burr 134. In the illustrated method, the radius of revolution of the burr 134 is so short that both on-axis and off-axis tissue is essentially removed. In effect, the burr 134 removes a small disc of tissue at this point. It should be noted that, during the tissue removal procedure, the removed tissue could be aspirated from the herniated disc 12' using an aspirator. Aspiration of the tissue can be accomplished via the cannula or through another cannula. Alternatively, as previously described, aspiration can be accomplished via the tissue removal probe 110, itself.

Figure 14E:
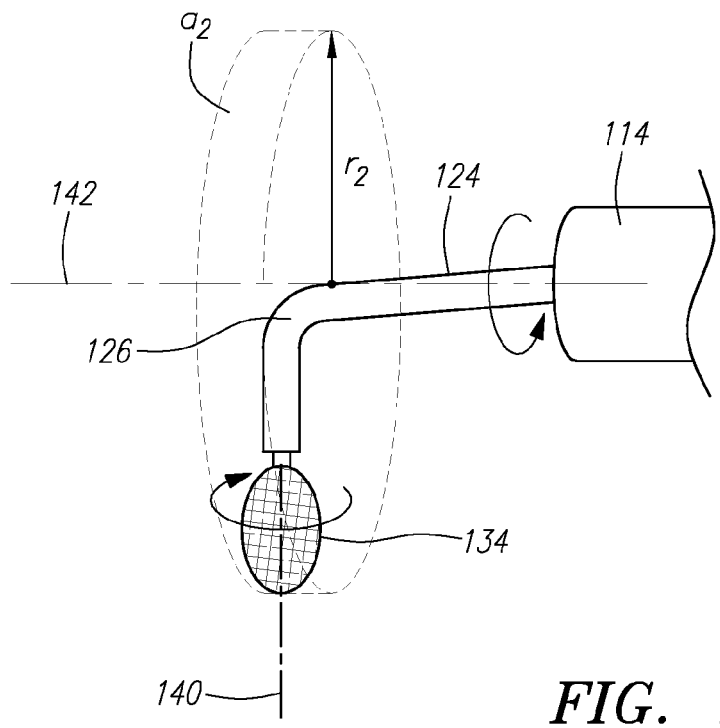

Next, the tissue removal probe 110 is further introduced through the cannula lumen 118 until the distal end 126 of the sleeve 124 deploys out from the exit port 120 of the cannula shaft 112 a second greater distance (FIG. 14D), which as described above, associates the burr 134 with a second greater radius of revolution $r_2$ around the rotational axis 142 of the sleeve 124. Again, the drive unit 104 is operated to rotate the burr 134 about is own rotational axis 140, while manually rotating the sleeve 124, which causes the burr 134 to scribe another larger arc $a_2$ around the rotational axis 142 of the sleeve 124 (FIG. 14E). As a result, a ring of tissue is removed by the rotating burr 134 along the larger arc $a_2$. Again, the sleeve 124 is rotated until the burr 134 scribes an entire circle around the rotational axis 142 of the sleeve 124. In this manner, a full circle of tissue is removed by the burr 134. The difference between the first and second radii and of revolution $r_1$ and $r_2$ is such that the disc of tissue removed by the burr 134 along the first arc $a_1$ is coextensive with the ring of tissue removed by the burr 134 along the second arc $a_2$. The steps illustrated in FIGS. 14D and 14E can be repeated to remove even larger discs of tissue.

Figure 14F:
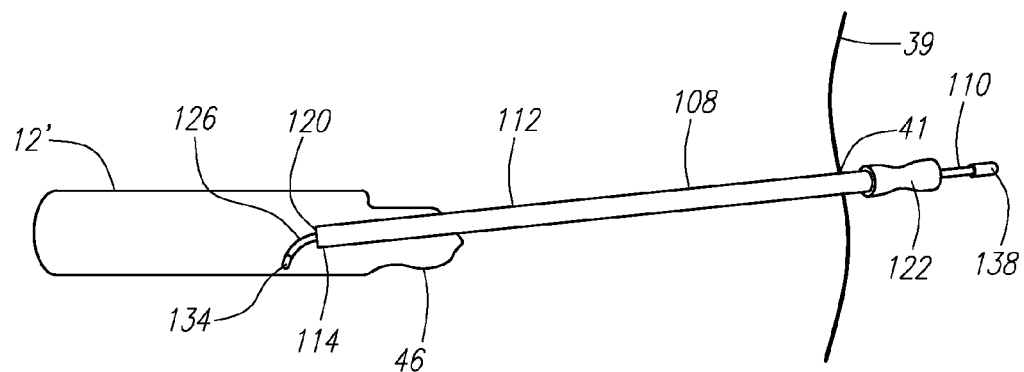
Figure 14G:
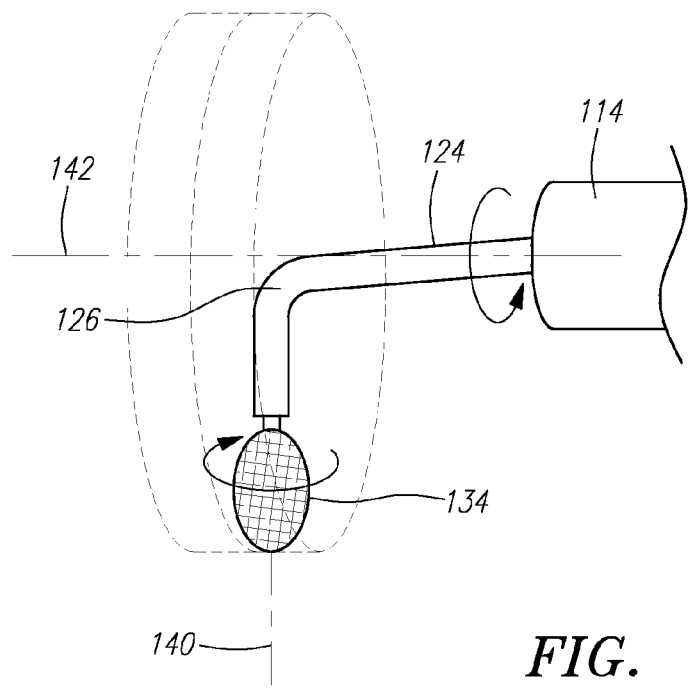

Next, the cannula 108 is displaced in the proximal direction, and the tissue removal probe 110 is retracted, so that the sleeve distal end 126 deploys out from the exit port 120 of the cannula shaft 112 the first distance (FIG. 14F). The steps illustrated in FIGS. 14B-14E are then repeated to remove another disc of tissue (FIG. 14G). In the illustrated method, the proximal displacement of the cannula 108 is such that the first and second discs of removed tissue are contiguous. As such, a cylinder of tissue is removed. A longer cylinder of tissue can be removed by repeating the steps illustrated in FIGS. 14F and 14G. After the discectomy has been completed (i.e., the herniated disc material has been removed, or in some cases, the entire herniated disc has been removed), the cannula 108, along with the tissue removal probe 110, is removed from the patient's body. Alternatively, prior to total removal of the cannula 108, the tissue removal probe 110 can be removed, and a therapeutic media, such as a drug or disc replacement material can be delivered through the cannula lumen 118 into the disc 12'.

Figure 15:
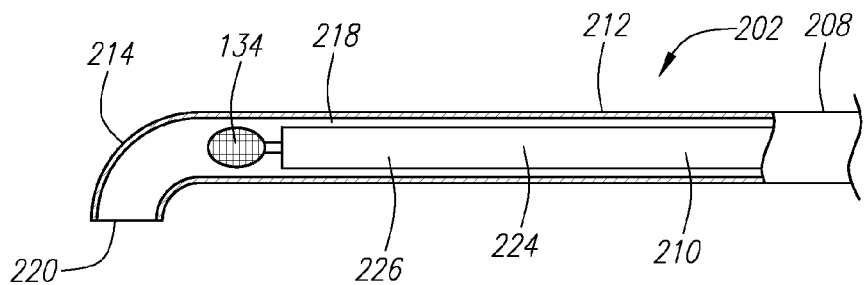
FIG. 15 is a partially cutaway side view of the distal end of another tissue removal probe that can be used in the tissue removal system of FIG. 8, particularly showing the tissue removal element retracted within the probe shaft.
Figure 16:
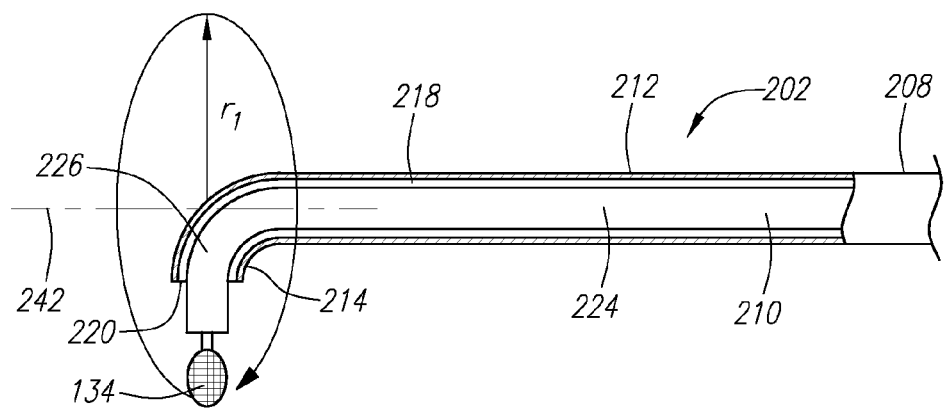
FIG. 16 is a partially cutaway side view of the distal end of the probe of FIG. 15, particularly showing the tissue removal element partially deployed from the probe shaft.
Figure 17:
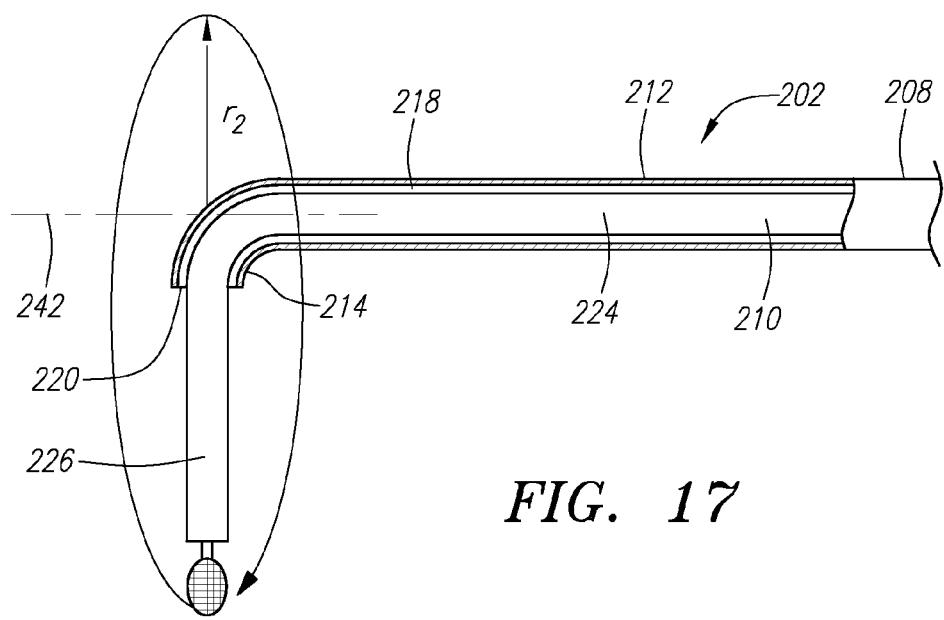
FIG. 17 is a partially cutaway side view of the distal end of the probe of FIG. 15, particularly showing the tissue removal element fully deployed from the probe shaft.

Although curved portion 144 of the sleeve distal end 126 is pre-shaped in order to create a radius of revolution r for the deployed burr 134, there are other means for bending the distal end of a sleeve as it deploys from a cannula. For example, FIGS. 15-17 illustrate a tissue removal assembly 202 that bends a deploying sleeve using the cannula, itself. In particular, the tissue removal assembly 202 comprises a cannula 208, which is similar to the previously described cannula 108, with the exception that it comprises a cannula shaft 212 with a curved distal end 214. In the illustrated embodiment, the distal end 214 of the cannula 208 assumes a ninety-degree curve. The tissue removal assembly 202 comprises a tissue removal probe 210 that is similar to the previously described tissue removal probe 110, with the exception that it comprises a sleeve 224 that does not have a pre-curved distal end. Instead, the entire sleeve 224 is configured to assume a straight configuration in its relaxed state.

As can be seen from FIG. 15, when confined within the cannula lumen 218, the sleeve 224 assumes a substantially straight configuration and conforms to the shape of the cannula shaft 212. As can be seen from FIGS. 16 and 17, the distal end 226 of the sleeve 224 bends when deployed from the distal end of the cannula shaft 112. That is, as it is deployed, the sleeve distal end 226 contacts the inner surface of the curved cannula distal end 214, thereby deflecting the sleeve distal end 226 as its exits the cannula lumen 218. Like the previously described sleeve 124, the sleeve is laterally resilient, such that it maintains its shape as it deploys from the exit port 220 at the distal end 214 of the cannula shaft 212.

As with the previously described sleeve distal end 126, the sleeve distal end 226 can be deployed from the exit port 220 of the cannula shaft 212 in stages. For example, the sleeve distal end 226 can be deployed a particular distance from exit port 220, so that the burr 134 defines a particular radius of revolution $r_1$ (shown in FIG. 16) around the rotational axis 242 of the sleeve 224. The sleeve distal end 226 can be deployed a second greater distance from the exit port 220, so that the burr 134 defines a second greater particular radius of revolution $r_2$ (shown in FIG. 17) around the rotational axis 242 of the sleeve 224. Thus, it can be appreciated that radius of revolution r of the burr 134 can be adjusted simply by displacing the sleeve 224 within the cannula lumen 218.

Operation of the tissue removal assembly 202 in removing soft tissue is similar to the operation of the previously described tissue removal assembly 102, and will thus, not be further described.

As another example, FIGS. 30-33 illustrate a tissue removal assembly 252 that has a sleeve with steering functionality. In particular, the tissue removal assembly 252 comprises the previously described cannula 108, and a tissue removal probe 260 that is similar to the previously described tissue removal probe 110, with the exception that it does not have a pre-curved distal end, but instead, comprises a pair of pull wires 254 (shown in FIG. 31) extending through a respective pair of pull wire lumens 256 contained within the sleeve 124. The distal ends of the pull wires 254 are mounted to the distal tip of the sleeve 124 in a suitable manner. As can be seen from FIG. 30, when confined within the cannula lumen 218, the sleeve 124 assumes a substantially straight configuration and conforms to the shape of the cannula shaft 112. As can be seen from FIGS. 32 and 33, the distal end 126 of the sleeve 124, when deployed from the exit port 120 of the cannula shaft 112, bends in one direction when one of the pull wires 254 is pulled.

As with the previously described tissue removal probe 110, the sleeve distal end 126 can be deployed from the exit port 120 of the cannula shaft 112 in stages. For example, the sleeve distal end 126 can be deployed a first distance from exit port 120 and one of the pull wires 254 pulled to bend the sleeve distal end 126, so that the burr 134 defines a particular radius of revolution $r_1$ (shown in FIG. 32) around the rotational axis 142 of the sleeve 124. The sleeve distal end 126 can be deployed a second greater distance from the exit port 120 and the pull wire 254 pulled to bend the sleeve distal end 126 again, so that the burr 134 defines a second greater particular radius of revolution $r_2$ (shown in FIG. 33) around the rotational axis 142 of the sleeve 124. Thus, it can be appreciated that radius of revolution r of the burr 134 can be adjusted simply by displacing the sleeve 124 within the cannula lumen 118 and pulling one of the pull wires 254 to bend the sleeve distal end 126.

Operation of the tissue removal assembly 252 in removing soft tissue is similar to the operation of the previously described tissue removal assembly 102, with the exception that the pull wires 254 are used to actively bend the distal end 126 of the sheath 124.

Alternatively, as illustrated in FIGS. 34A-34F, the tissue removal assembly 252 may be used in a different manner to remove soft tissue from an anatomical body, and in particular, in performing a discectomy on a herniated intervertebral disc. This alternative method is accomplished by bending the distal end 126 of the sleeve 124 in opposite directions using the pull wires 254, while rotating the burr 134, thereby removing tissue in an arc that is coplanar with the plane of the axis 142. In this case, a layer of tissue is removed in a plane that is parallel with the flat sides of the herniated disc.

Figure 34A:
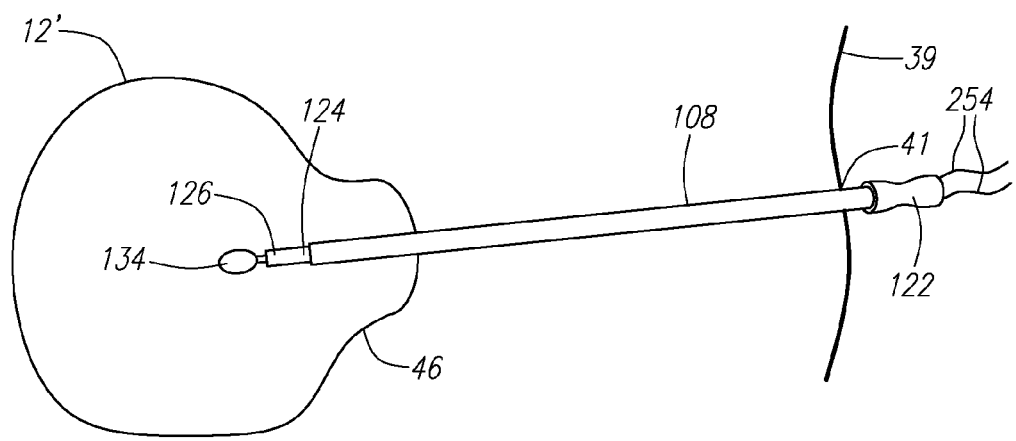
FIGS. 34A-34D are perspective views showing a method of using the tissue removal system of FIG. 8, with the tissue removal probe of FIG. 30, to remove tissue within a herniated intervertebral disc.
Figure 34B:
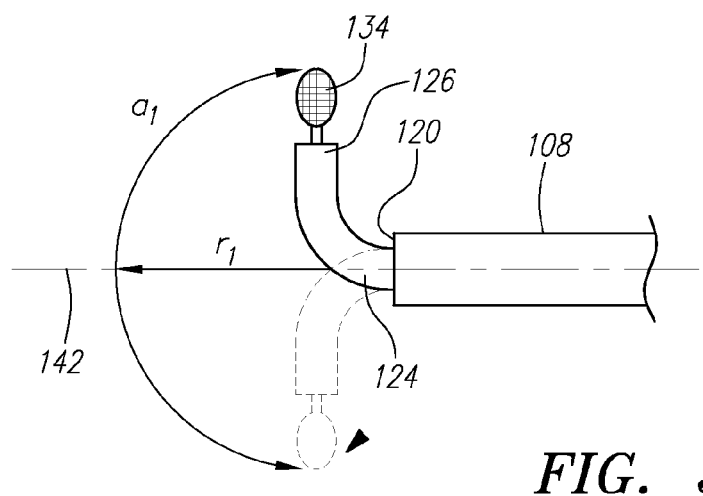
Figure 34C:
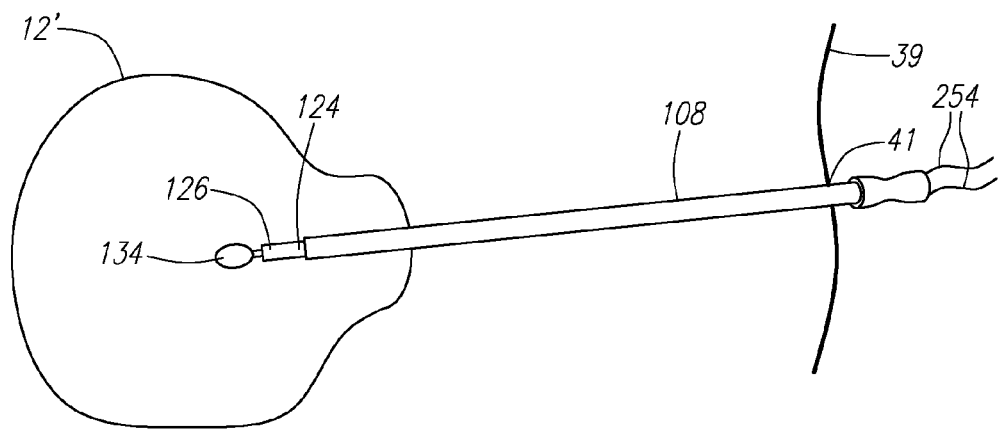

In particular, after the cannula 108 is introduced into the herniated disc 12' in the same manner previously illustrated in FIG. 14A, the tissue removal probe 260 is introduced through the cannula lumen 118 until the distal end 126 of the sleeve 124 deploys out from exit port 120 of the cannula shaft 112 a first distance (FIG. 34A), which associates the burr 134 with a first radius of curvature $r_1$ (shown in FIG. 34B). Next, the proximal adapter 138 of the tissue removal probe 210 is mated to the drive unit (shown in FIG. 8), which is then operated to rotate the burr 134 about is own rotational axis 140. At the same time, the distal end 126 of the sleeve 124 is bent in one direction by pulling one of the pull wires 254 (shown in FIG. 34A), which causes the rotating burr 134 to scribe a ninety degree arc $a_1$ (as measured from the longitudinal axis 142) around the distal tip of the sleeve 124 (FIG. 34B). Next, the distal end 126 of the sleeve 124 is bent in the opposite direction by pulling the other pull wire 254, which causes the rotating burr 134 to scribe a one hundred eighty degree arc $a_1$ (ninety degrees above the longitudinal axis 142 and ninety degrees below the longitudinal axis 142) around the distal tip of the sleeve 124 (shown in phantom in FIG. 34B). In this manner, a semi-circle of tissue is removed by the burr 134. In the illustrated method, the radius of curvature of the burr 134 is so short that a solid radial sector of tissue is removed. As with the previous methods, the remove tissue can optionally be aspirated.

Figure 34D:
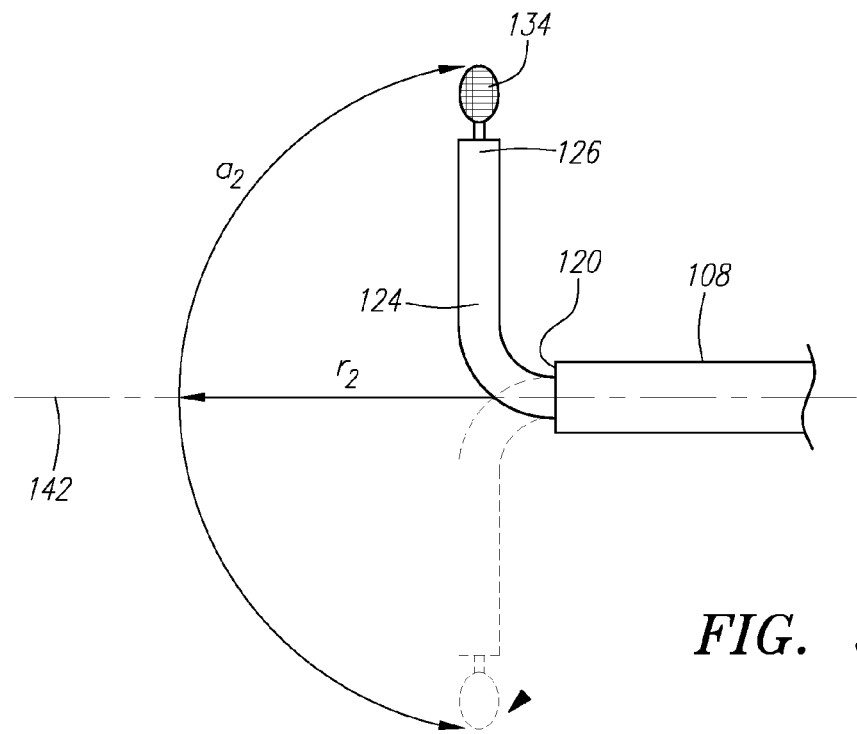

Next, the tissue removal probe 210 is further introduced through the cannula lumen 118 until the distal end 126 of the sleeve 124 deploys out from the exit port 120 of the cannula shaft 112 a second greater distance (FIG. 34C), which associates the burr 134 with a second greater radius of curvature $r_2$ (shown in FIG. 34D). Again, the drive unit 104 is operated to rotate the burr 134 about is own rotational axis 140, while bending the distal end 126 of the sleeve 124 in one direction using the first pull wire 254 (shown in FIG. 34C), which causes the burr 134 to scribe another larger ninety degree arc $a_2$ around the distal tip of the sleeve 124 (FIG. 34D). Next, the distal end 126 of the sleeve 124 is bent in the opposite direction by pulling the other pull wire 254, which causes the rotating burr 134 to scribe a one hundred eighty degree arc $a_2$ around the distal tip of the sleeve 124 (shown in phantom in FIG. 34D). In this manner, a semi-circlular ring of tissue is removed by the burr 134.

The difference between the first and second radii and of curvature $r_1$ and $r_2$ is such that the radial sector of tissue removed by the burr 134 along the first arc $a_1$ is coextensive with the semi-circular ring of tissue removed by the burr 134 along the second arc $c_2$. The steps illustrated in FIGS. 34C and 34D can be repeated to remove even larger discs of tissue.

After the discectomy has been completed (i.e., the herniated disc material has been removed, or in some cases, the entire herniated disc has been removed), the cannula 108, along with the tissue removal probe 110, is removed from the patient's body. Alternatively, prior to total removal of the cannula 108, the tissue removal probe 260 can be removed, and a therapeutic media, such as a drug or disc replacement material can be delivered through the cannula lumen 118 into the disc 12'.

Figure 18:
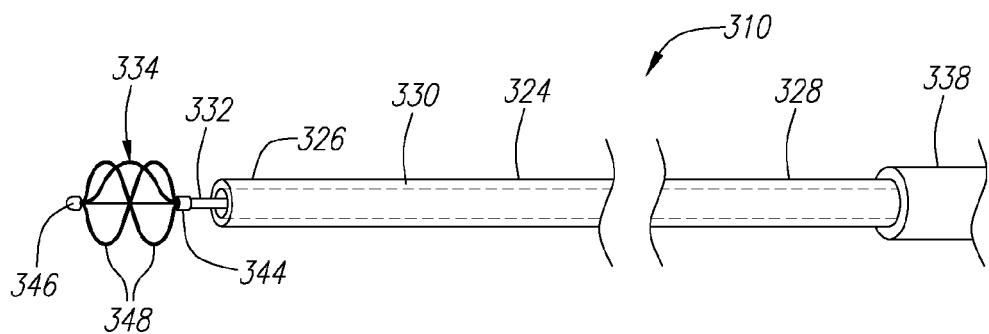
FIG. 18 is perspective view of still another tissue removal probe that can be used in the system of FIG. 8.
Figure 19:
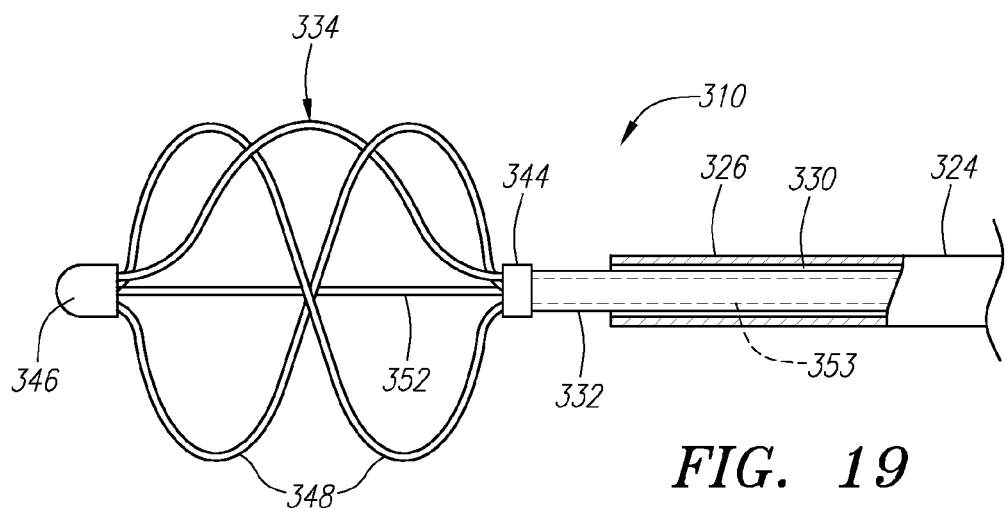
FIG. 19 is a partially cut-away side view of the distal end of the probe of FIG. 18, particularly showing a tissue removal element.

Referring now to FIGS. 18 and 19, another tissue removal probe 310 that can alternatively be used in the tissue removal system 100 will be described. The tissue removal probe 310 comprises a sleeve 324 having a distal end 326 and a proximal end 328, and a lumen 330 (shown in phantom in FIG. 18) extending through the sleeve 324. The tissue removal probe 310 further comprises a drive shaft 332 rotatably disposed within the sleeve lumen 330 and a rotatable tissue removal element, and in particular, a rotatable cutting basket 334, mounted to the distal end of the drive shaft 332. The tissue removal probe 310 further comprises a proximal adapter 338 mounted to the proximal end 328 of the sleeve 324. The proximal adapter 338 is configured to be mated with the drive cable 106, thereby providing a means for rotatably coupling the drive unit 104 to the proximal end of the drive shaft 332. Thus, operation of the drive unit 104 will rotate the drive shaft 332, which, in turn, will rotate the cutting basket 334 about its rotational axis 340. Like the tissue removal probe 110, the tissue removal probe 310 can be rotatably disposed within the lumen 118 of the cannula 108, so that the cutting basket 334 can be alternately deployed from and retracted into the distal end 114 of the cannula shaft 112.

The cutting basket 334 comprises a base member 344, a distal hub 346, and a plurality of filaments 348 proximally affixed to the base member 344 and distally affixed to the distal hub 346. The base member 344 is mounted to the distal end of the drive shaft 332 using suitable means, such as soldering or welding. The distal hub 346 is preferably rounded, such that only lateral tissue removal is achieved, and inadvertent tissue trauma distal to the cutting basket 334 is prevented. As shown in FIGS. 18 and 19, the shape of the filaments 348 is sinusoidal, although other shapes can be provided. Although three filaments 348 are shown, the cutting basket 334 may include a different number of filaments 348. The filaments 348 are also interlaced or braided to provide the cutting basket 334 with a more integral structure.

Figure 20:
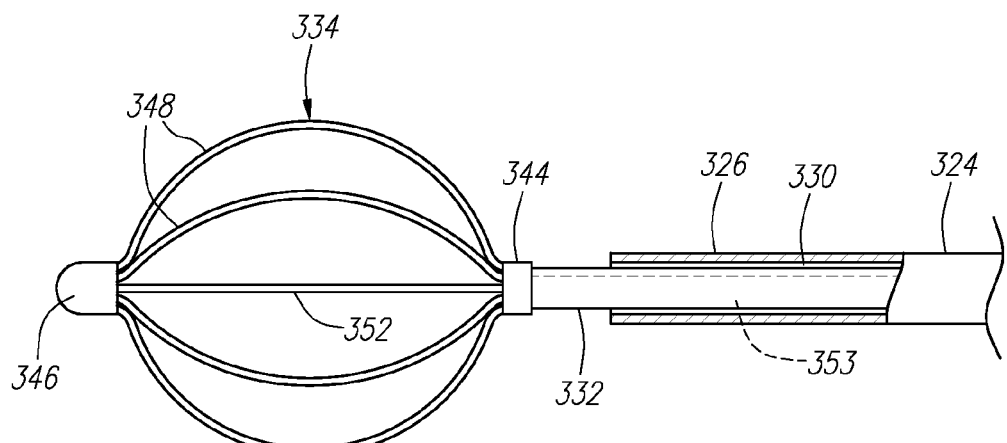
FIG. 20 is a partially cut-away side view of a variation of the distal end of the probe of FIG. 18, particularly showing a variation of the tissue removal element.

In alternative embodiments, however, the filaments 348 can configured differently. For example, FIG. 20 illustrates an alternative cutting basket 354, wherein the filaments 348, the proximal and distal ends of which are mounted to the base member 344, thereby affixing the filaments 348 at the proximal end of the cutting basket 334. The filaments 348 are affixed at the distal end of the cutting basket 334 by looping the filaments 348 through the distal hub 346.

Whichever filament configuration is used, the cross-sectional shape of each filament 348 can be circular, rectangular, elliptical, or other customized shapes. As can be appreciated, the large spaces between the filaments 348 prevent, or at the least minimize, the build-up of tissue on the cutting basket 334. If bone tissue is to be removed, the filaments 348 are preferably made from a tough material, such as steel or other alloys, so that it could penetrate or cut into a bone structure without being damaged. The stiffness of the filaments 348 are preferably selected so that the cutting basket 334 is stiff enough to cut, deform, and/or compact target bone tissue. In the case where soft tissue is to be removed, the filaments 348 may likewise be composed of a soft material. In any event, the material from which the filaments 348 are made are resilient, such that cutting basket 334 assumes a low profile while residing within the cannula lumen 330, and is free to assume an expanded profile when deployed outside of the cannula lumen 330. In the illustrated embodiment, the cutting basket 334 is 1 cm in length and ½ cm in diameter.

In some embodiments, the filaments 348 have sharp edges, thereby providing bone, disc or soft tissue cutting/drilling capability. In other embodiments, the cutting basket 334 includes abrasive particles, such as diamond dusts, disposed on surfaces of the filaments 348, for cutting, digging, and/or sanding against target bone, disc or soft tissue. The filaments 348 are connected between the base member 344 and distal hub 346 and drive shaft 332 using means, such as a welding, brazing, or glue, depending on the materials from which the distal hub, filaments, and drive shaft 332 are made. Alternatively, the filaments 348 are connected between the distal hub 346 and drive shaft 332 by a snap-fit connection, a screw connection, or otherwise an interference-fit connection.

The tissue ablation probe 310 optionally comprises a guidewire 352 that extends through a lumen 353 (shown in phantom) within the drive shaft 332, and is mounted to the distal hub 346 of the cutting basket 334. In this manner, the lateral movement of the cutting basket 334 during operation is limited.

Figure 21:
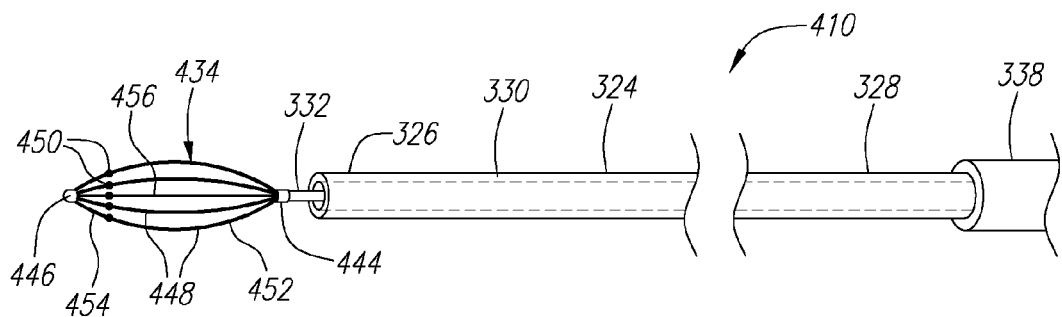
FIG. 21 is perspective view of yet another tissue removal probe that can be used in the system of FIG. 8.
Figure 22A:
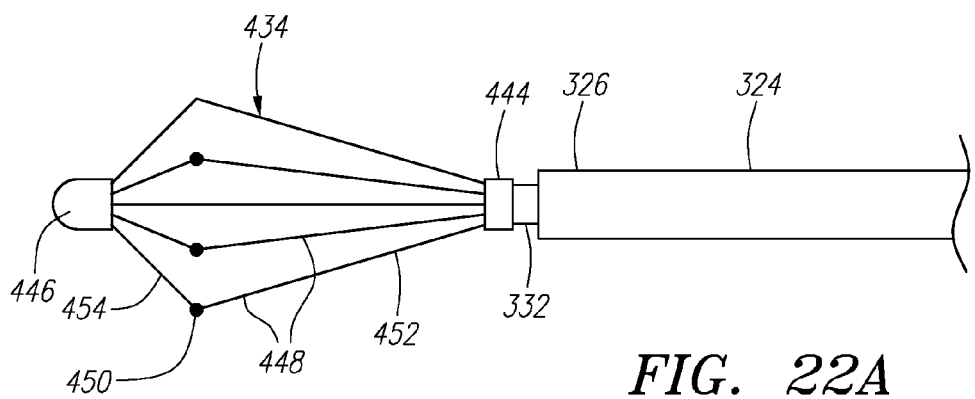
FIGS. 22A-22D are side views of the distal end of the probe of FIG. 21, particularly showing a transformation of the probe from a tissue-cutting device to a tissue-grasping device.
Figure 22B:
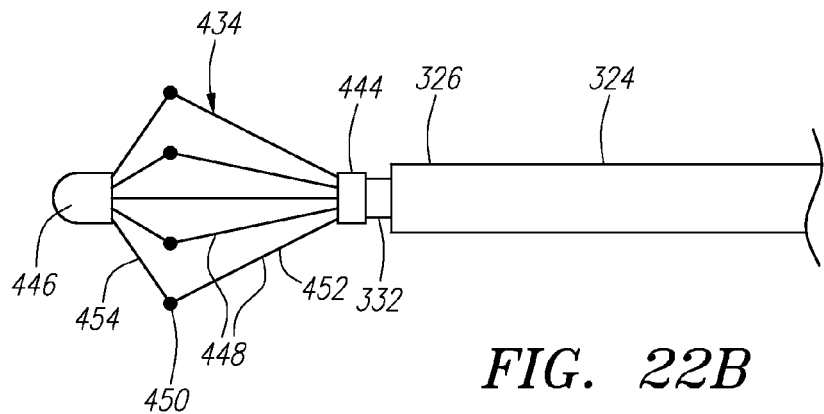
Figure 22C:
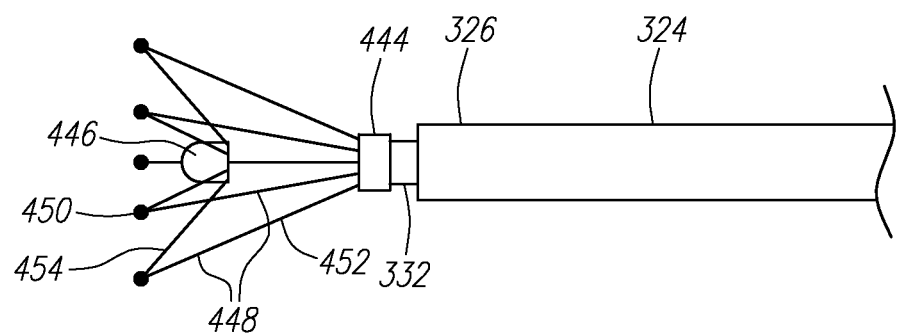
Figure 22D:
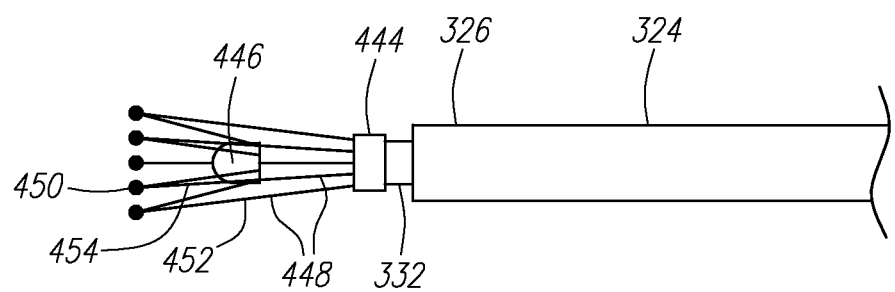

Referring now to FIG. 21, still another tissue removal probe 410 that can alternatively be used in the tissue removal system 100 will be described. The tissue removal probe 410 is similar to the previously described tissue removal probe 310 in that it comprises the sleeve 324, drive shaft 332, and proximal adapter 338. The tissue removal probe 410 differs from the tissue removal probe 310 in that it comprises a tissue removal device, and in particular, a cutting basket, that can be transformed between a tissue-cutting device and a tissue grasper.

In particular, the cutting basket 434 comprises a base member 444, a distal hub 446, and a plurality of filaments 448 proximally affixed to the base member 444 and distally affixed to the distal hub 446. The base member 444 is mounted to the distal end of the drive shaft 332 using suitable means, such as soldering or welding. The distal hub 446 is preferably rounded, such that only lateral tissue removal is achieved, and inadvertent tissue trauma distal to the cutting basket 434 is prevented. The filaments 448 may have the same composition as the previously described filaments 448.

Each filament 448, however, has a hinge point 450 that divides the filament 448 into a proximal filament segment 452 and a distal filament segment 454. As shown in the progression illustrated in FIGS. 22A-22D, pulling the distal hub 446 in the proximal direction causes the distal end of the cutting basket 434 to invert into the proximal end of the cutting basket 434. That is, the distal filament segments 454 fold around the hinge points 450 towards the proximal filament segments 452, transforming the folded filaments 448 into tissue-grasping arms, with the hinge points 450 forming the most distal points of the arms. Notably, the hinge points 450 are located distal to the midpoints of the filaments 448 (i.e., the distal filament segments 454 are shorter than the proximal filament segments 452). In this manner, the resulting tissue-grasping arms are relatively short, and therefore have a greater resistance to lateral bending when grasping tissue.

The actuating device takes the form of a pull wire 456 that extends through the lumen 353 in the drive shaft 332, attaching to the distal hub 446. Thus, when the pull wire 456 is pulled, the cutting basket 434 is transformed from a tissue-cutting device to a tissue-grasping device. When the pull wire 456 is relaxed, the tissue-grasping device (due to its resiliency) reverts back to a tissue-cutting device. That is, the distal filament segments 454 will fold back around the hinge points 450 away from the proximal filament segments 452, transforming the filaments 448 into tissue-cutting filaments.

Figure 23:
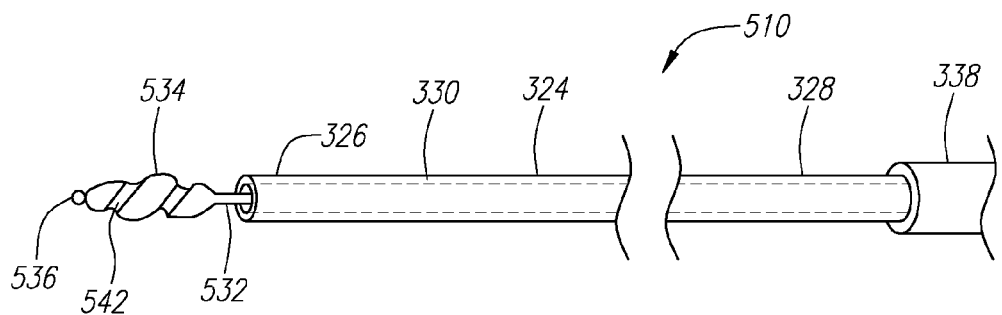
FIG. 23 is perspective view of yet another tissue removal probe that can be used in the system of FIG. 8.
Figure 24:
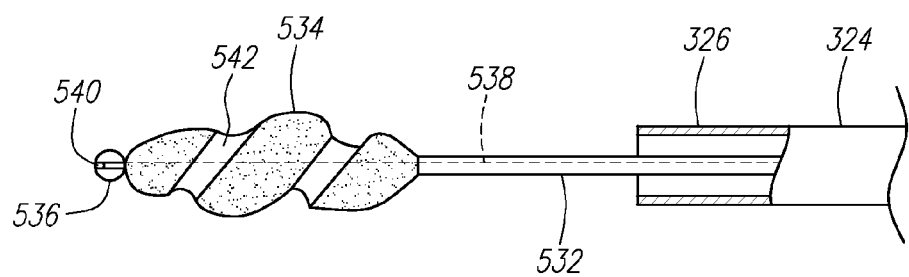
FIG. 24 is a partially cut-away side view of the distal end of the probe of FIG. 23.

Referring now to FIGS. 23 and 24, yet another tissue removal probe 510 that can alternatively be used in the tissue removal system 100 will be described. The tissue removal probe 510 is similar to the previously described tissue removal probe 310 in that it comprises the sleeve 324 and proximal adapter 338. The tissue removal probe 510 differs from the tissue removal probe 310 in that it has tissue irrigating functionality and minimizes inadvertent trauma to distal tissue, otherwise caused by a tissue removal element 534.

In particular, the tissue removal probe 510 comprises a drive shaft 532, which is composed of a rigid material, such as stainless steel, and has a distal end with a non-traumatic blunt tip 536. The blunt tip 536 prevents the tissue removal element 534 from abrading or harming distal tissue during use. In the illustrated embodiment, the blunt tip 536 has a spherical shape. In alternative embodiments, however, the blunt tip 536 can have other shapes as well. The drive shaft 332 further comprises an irrigation lumen 538 (shown in phantom) that terminates in an irrigation port 540 at the blunt tip 536. As previously described, irrigation fluid can be delivered through the irrigation lumen 538 and out of the irrigation port 540 in order to cool the drive shaft 332 and/or tissue removal element 534, as well as to wash debris at the target site. The irrigation lumen 538 can alternatively be used as a guidewire lumen.

The tissue removal element 534 is formed on the distal end of the drive shaft 332 just proximal to the blunt tip 536. In the illustrated embodiment, the tissue removal device 534 comprises an ellipsoidal burr, although other geometrically shaped burrs can be used. Unlike a cutting basket, the cross-section of the burr 534 is relatively more solid, thereby providing more stiffness. Such configuration is advantageous in that it allows cutting and/or abrading of stiff materials without deforming. In the illustrated embodiment, the burr 534 includes abrasive particles, such as diamond dusts, that are disposed on the surface of the burr 534. In other embodiments, instead of having diamond dusts, parts of the surface of the burr 534 can be removed to create an abrasive surface. The burr 534 further comprises a spiral cutting groove 542. During use, the groove 542 allows bone particles that have been removed to travel proximally and away from a target site.

Figure 25:
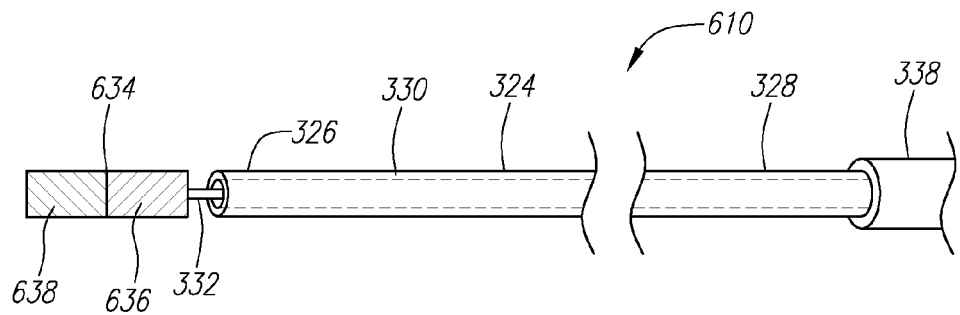
FIG. 25 is perspective view of yet another tissue removal probe that can be used in the system of FIG. 8.

Referring now to FIG. 25, yet another tissue removal probe 610 that can alternatively be used in the tissue removal system 100 will be described. The tissue removal probe 610 is similar to the previously described tissue removal probe 310 in that it comprises the sleeve 324, drive shaft 332, and proximal adapter 338. The tissue removal probe 610 differs from the tissue removal probe 310 in that it comprises a tissue removal element 634 with counter-pitched grooves.

In particular, the tissue removal element 634 is mounted to the distal end of the drive shaft 332, and takes the form of a cylindrically-shaped burr with proximal spiral cutting grooves 636 and distal spiral cutting grooves 638. The respective proximal and distal grooves 636 and 638 are oppositely pitched, such the removed tissue is force to travel along the grooves 636/638 towards the center of the burr 634 when rotated in a particular direction (in this case, clockwise if looking down the distal end of the burr 634). In this manner, the removed tissue will tend to be collected in one place, thereby making aspiration of the tissue easier.

Figure 26:
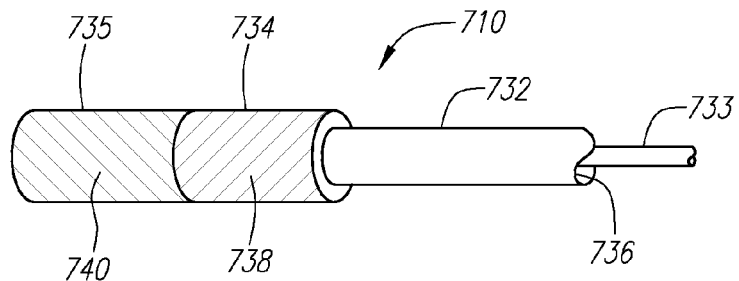
FIG. 26 is a partially cut-away side view of the distal end of yet another tissue removal probe that can be used in the system of FIG. 8.

Referring now to FIG. 26, yet another tissue removal probe 710 that can alternatively be used in the tissue removal system 100 will be described. The tissue removal probe 710 is similar to the previously described tissue removal probe 610 with the exception that two counter-rotating burrs are used.

In particular, the tissue removal probe 710 comprises an outer drive shaft 732 with a lumen 736, and an inner drive shaft 733 disposed within the outer drive shaft lumen 736. As such, the drive shafts 732 and 733 are independent, and can thus be rotated in opposite directions or the same direction. The tissue removal probe 710 further comprises proximal and distal removal elements 734 and 735 in the form of cylindrical burrs mounted to the distal ends of the respective drive shafts 732 and 733. The cylindrical burrs 734 and 735 are collinear and coextensive with each other, so that they can operate as a contiguous tissue removal device. Spiral cutting grooves 738 and 740 are formed in the surfaces of the respective burrs 734 and 735 In the illustrated embodiment, the absolute pitch of the spiral grooves 738 on the proximal burr 734 is the same as the absolute pitch on the distal burr 735. The grooves 738/740, however, are pitched in the opposite direction. Thus, rotation of the proximal burr 734 in one direction (by rotating the outer drive shaft 732 in that direction), and rotation of the distal burr 735 in the opposite direction (by rotating the inner drive shaft 733 in that direction) will stabilize the tissue removal probe 710 as it is laterally cutting through tissue, e.g., bone tissue. That is, the counter-rotating burrs 734/735 prevents, or at least minimizes, the tendency of the tissue removal probe 710 to stray from its intended cut path.

Alternatively, the burrs 734/735 can be rotated in the same direction, preferably in a direction that forces the removed tissue to travel along the grooves 738/740 of the respective burrs 734/735 towards the interface between the burrs 734/735. In this manner, the removed tissue will tend to be collected in one place, thereby making it more easily aspirated. Thus, it can be appreciated that the independence of the outer and inner drive shafts 732/733, allows the respective burrs 734/735 to be selectively rotated in opposite directions or rotated in the same direction.

Figure 27:
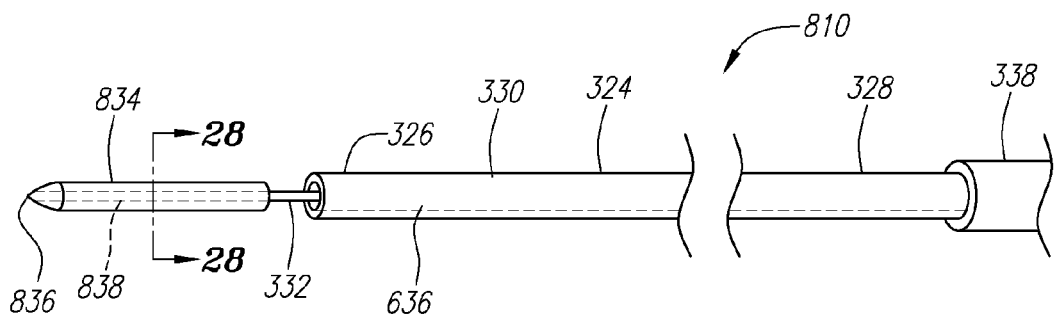
FIG. 27 is perspective view of yet another tissue removal probe that can be used in the system of FIG. 8.

Referring now to FIG. 27, yet another tissue removal probe 810 that can alternatively be used in the tissue removal system 100 will be described. The tissue removal probe 810 is similar to the previously described tissue removal probe 310 in that it comprises the sleeve 324, drive shaft 332, and proximal adapter 338. The tissue removal probe 810 differs from the tissue removal probe 310 in that it comprises a tissue removal element 834 configured to drill holes through bone, whereas the tissue removal element of the tissue removal probe 310, as well as those subsequently described in tissue removal probes 410, 510, 610, and 710, lend itself well to the lateral removal of hard bone tissue, e.g., during laminectomy and laminotomy procedures.

Figure 28:
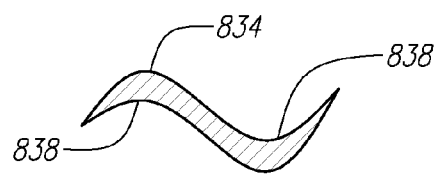
FIG. 28 is a cross-sectional view of the probe of FIG. 27, taken along the line 28-28.

In particular, the tissue removal element 834 takes the form of a drill bit mounted at the distal end of the drive shaft 332. The drill bit 834 has a sharp distal tip 836 that allows the rotating drill bit 834 to penetrate or shape bone tissue. In the illustrated embodiment, the drill bit 834 has a length that is between ¼ and 1 inch, and a diameter that is between 1/100 and ½ inch. The drill bit 834 includes two fluted cutting grooves 838 that extend down opposite sides of the drill bit 834, as shown in FIG. 28.

Figure 29:
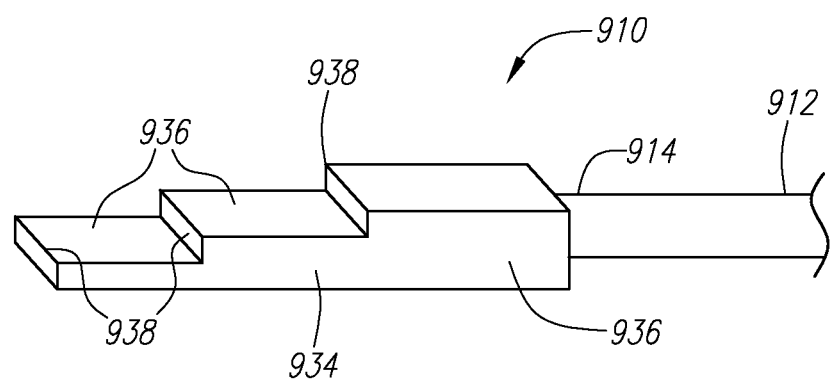
FIG. 29 is perspective view of yet another tissue removal probe that can be used in the system of FIG. 8.
Figure 30:
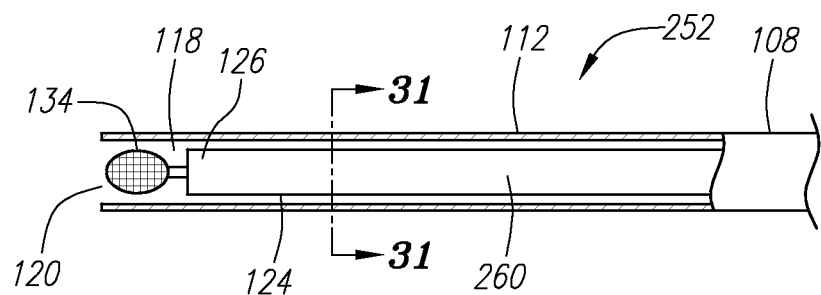
FIG. 30 is a partially cutaway side view of the distal end of still another tissue removal probe that can be used in the tissue removal system of FIG. 8, particularly showing the tissue removal element retracted within the probe shaft.
Figure 31:
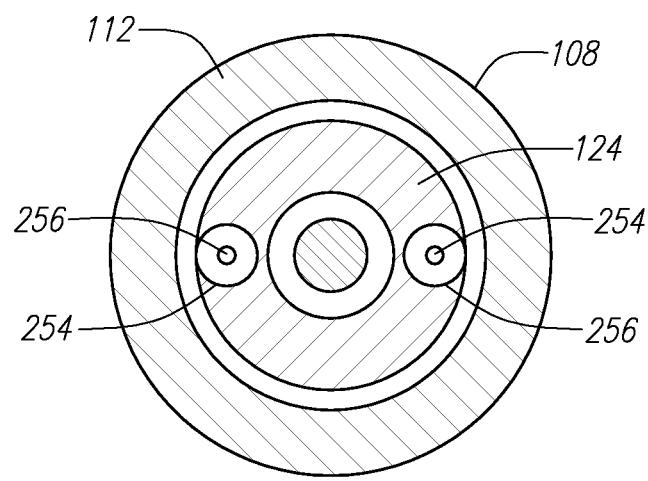
FIG. 31 is a cross-sectional view of the distal end of the tissue removal probe of FIG. 30, taken along the line 31-31.
Figure 32:
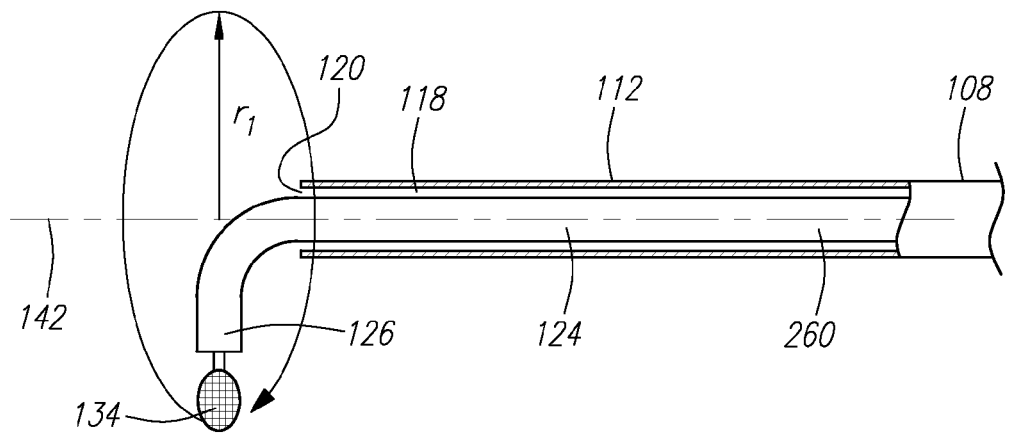
FIG. 32 is a partially cutaway side view of the distal end of the probe of FIG. 30, particularly showing the tissue removal element partially deployed from the probe shaft.
Figure 33:
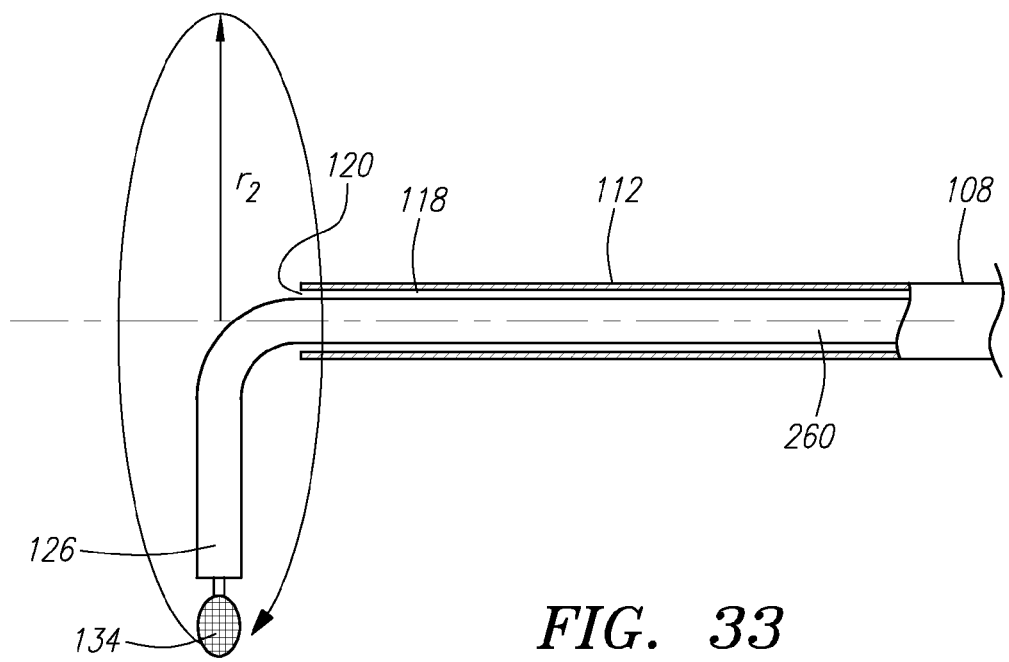
FIG. 33 is a partially cutaway side view of the distal end of the probe of FIG. 30, particularly showing the tissue removal element fully deployed from the probe shaft.

Referring now to FIG. 29, yet another tissue removal probe 910 that can alternatively be used in the tissue removal system 100 will be described. Unlike in the previously described embodiments, which have rotatable tissue removal elements, the tissue removal probe 910 comprises a reciprocating tissue removal element. In particular, the tissue removal probe 910 comprises a rigid drive shaft 912 having a distal end 914, and a tissue removal element 934 formed on the distal end 914 of the drive shaft 912. The tissue removal element 934 comprise a block 936 with a series of cascading tissue-cutting notches 938 longitudinally formed along the block 934. As a result, a series of sharp leading edges 940 are formed along the block 934. In the illustrated embodiment, the block 936 has a rectangular cross-section.

Thus, it can be appreciated that the tissue removal element 934 can be placed within a hole or groove in a bone, and reciprocatably moved to remove bone tissue from the bone, thereby enlarging the hole. A motor can be configured to apply a hammering motion (i.e., a forward and rearward motion) to drive the shaft 912.

Although particular embodiments of the present invention have been shown and described, it should be understood that the above discussion is not intended to limit the present invention to these embodiments. It will be obvious to those skilled in the art that various changes and modifications may be made without departing from the spirit and scope of the present invention. In addition, an illustrated embodiment needs not have all the aspects or advantages of the invention shown. An aspect or an advantage described in conjunction with a particular embodiment of the present invention is not necessarily limited to that embodiment and can be practiced in any other embodiments of the present invention even if not so illustrated. Thus, the present invention is intended to cover alternatives, modifications, and equivalents that may fall within the spirit and scope of the present invention as defined by the claims.

What is claimed:

1. A tissue removal device, comprising:
a drive shaft defining an axial lumen;
a blunt, non-traumatic tip coupled to a distal end of the drive shaft, the tip having an aperture there through in fluid communication with the drive shaft lumen;
a tissue removal member carried on the drive shaft proximal to the tip;
a proximal adapter coupled to the elongated tubular member, the proximal adapter configured for operative coupling with a drive unit such that the drive shaft may be rotated by the drive unit, wherein the proximal adapter is further configured for coupling with an irrigation source to thereby place the irrigation source in fluid communication with the drive shaft lumen and tip aperture.

2. A tissue removal assembly, comprising:
a cannula defining a lumen;
an elongated tubular member defining a lumen, wherein the tubular member is disposed within the cannula lumen;
a drive shaft defining a lumen, wherein the drive shaft is rotatably disposed within the elongated tubular member;
a blunt, non-traumatic tip coupled to a distal end of the drive shaft, the tip having an aperture there through in fluid communication with the drive shaft lumen;
a tissue removal member carried on the drive shaft proximal to the blunt tip;
a proximal adapter coupled to a proximal end of the elongated tubular member;
a drive unit operatively coupled to the drive shaft via the proximal adapter, such that the drive shaft may be rotated by the drive unit; and
an irrigation source in fluid communication with the drive shaft lumen and tip aperture.

3. The assembly of claim 2, wherein the blunt tip is spherical.

4. The assembly of claim 2, wherein the tissue removal member comprises an abrasive burr.

5. The assembly of claim 4, the abrasive burr comprising a spiral cutting groove.

6. A tissue removal device, comprising:
a sleeve having a lumen;
a proximal adapter at the proximal end of the sleeve;
a drive shaft disposed within the lumen of the sleeve;
a non-traumatic tip coupled to a distal most end of the tissue removal device; and
a tissue removal member on the drive shaft proximal to the tip.

7. The assembly of claim 6, wherein the tissue removal member comprises an ellipsoidal burr and the ellipsoidal burr comprises a spiral cutting groove.

8. The assembly of claim 6, wherein the drive shaft comprises a lumen.

9. The assembly of claim 8, wherein the lumen of the drive shaft is configured to be in fluid communication with an irrigation source.

* * * * *